(12) United States Patent
Yamauchi

(10) Patent No.: US 8,133,742 B2
(45) Date of Patent: Mar. 13, 2012

(54) METHOD FOR MEASURING IMMUNOCHROMATO TEST PIECE

(75) Inventor: Kazunori Yamauchi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 247 days.

(21) Appl. No.: 12/516,412

(22) PCT Filed: Dec. 3, 2007

(86) PCT No.: PCT/JP2007/073293
§ 371 (c)(1),
(2), (4) Date: Jul. 1, 2009

(87) PCT Pub. No.: WO2008/084607
PCT Pub. Date: Jul. 17, 2008

(65) Prior Publication Data
US 2010/0087010 A1    Apr. 8, 2010

(30) Foreign Application Priority Data
Jan. 9, 2007   (JP) .............................. P2007-001662

(51) Int. Cl.
*G01N 21/78* (2006.01)
(52) U.S. Cl. ...................................... 436/514
(58) Field of Classification Search ........................ None
See application file for complete search history.

(56) References Cited

U.S. PATENT DOCUMENTS

| | | | | |
|---|---|---|---|---|
| 5,885,526 A | * | 3/1999 | Chu | 422/424 |
| 5,889,585 A |   | 3/1999 | Markart | |
| 5,914,241 A | * | 6/1999 | Valkirs | 435/7.4 |
| 7,955,791 B2 | * | 6/2011 | Dinello et al. | 435/4 |
| 2001/0000175 A1 |   | 4/2001 | Kurane et al. | |
| 2002/0173050 A1 | * | 11/2002 | DiNello et al. | 436/518 |
| 2003/0054567 A1 |   | 3/2003 | Miyoshi et al. | |
| 2003/0100128 A1 | * | 5/2003 | Kenjyou et al. | 436/518 |
| 2005/0130322 A1 | * | 6/2005 | Beesley et al. | 436/518 |
| 2006/0231421 A1 | * | 10/2006 | Diamond et al. | 205/777.5 |
| 2010/0098587 A1 | * | 4/2010 | Miyoshi et al. | 422/70 |

FOREIGN PATENT DOCUMENTS

| | | |
|---|---|---|
| EP | 0994343   * | 9/1999 |
| EP | 1564546 A1 * | 8/2005 |
| JP | 8-15260 | 1/1996 |
| JP | 10-274624 | 10/1998 |
| JP | 11-83745 | 3/1999 |
| JP | 2001-141644 | 5/2001 |
| JP | 2001-221797 | 8/2001 |
| JP | 2001-289846 | 10/2001 |
| JP | 2003-4743 | 1/2003 |

(Continued)

*Primary Examiner* — N. Yang
*Assistant Examiner* — Richard Moerschell
(74) *Attorney, Agent, or Firm* — Drinker Biddle & Reath LLP

(57) ABSTRACT

After dropping a sample onto an immunochromatographic test strip, a change of absorbance at a first position on the immunochromatographic test strip is sensed by detecting reflected light while illuminating a measurement light on the first position, a change of absorbance at a second position at a downstream side of the first position on the immunochromatographic test strip is sensed by detecting reflected light while illuminating measurement light on the second position, and a coloration degree is corrected based on an elapsed time from the change of absorbance at the first position to the change of absorbance at the second position.

6 Claims, 34 Drawing Sheets

FOREIGN PATENT DOCUMENTS

| | | |
|---|---|---|
| JP | 2004-170217 | 6/2004 |
| JP | 2006-162496 | 6/2006 |
| JP | 2006-189317 | 7/2006 |
| JP | 2006-208386 | 8/2006 |
| WO | WO 02-25253 | 3/2002 |
| WO | WO 2004/046699 | 6/2004 |
| WO | WO 2004-077029 | 9/2004 |
| WO | WO 2004/077030 | 9/2004 |
| WO | WO 2007/007849 | 1/2007 |

* cited by examiner

Fig.13
(a)
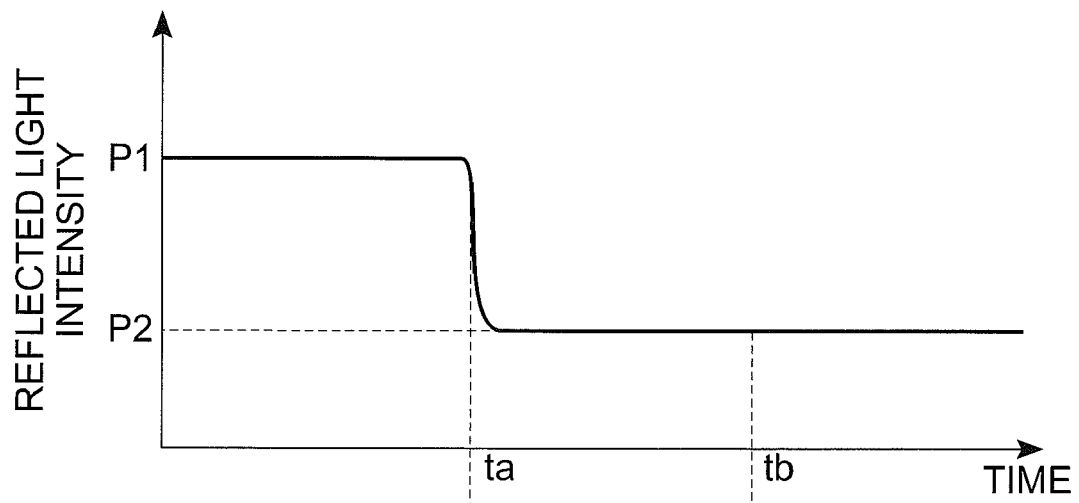
(b)
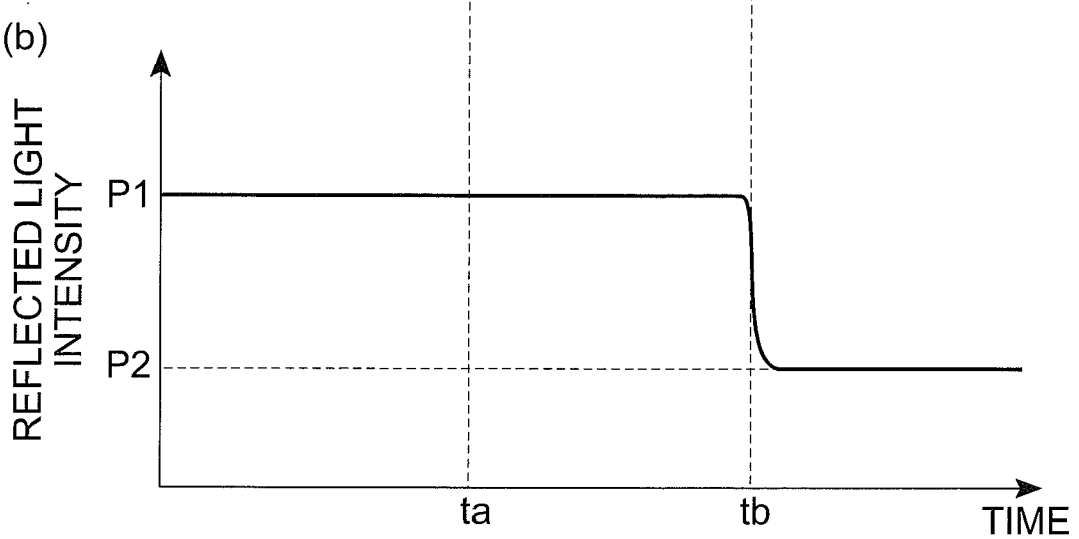

Fig.15

| IMMUNOCHROMATOGRAPHIC TEST STRIP NO. | ta[seconds] | tb[seconds] | tb-ta[seconds] | ABS₁ | CORRECTED ABS₁ |
|---|---|---|---|---|---|
| M1 | 12.82 | 74.82 | 62.00 | 0.2681 | 0.2812 |
| M2 | 11.51 | 78.49 | 66.98 | 0.2846 | 0.2797 |
| M3 | 12.34 | 71.74 | 59.40 | 0.2586 | 0.2810 |
| M4 | 14.05 | 84.46 | 70.41 | 0.3079 | 0.2907 |
| M5 | 11.49 | 78.10 | 66.61 | 0.2601 | 0.2566 |
| M6 | 11.13 | 72.94 | 61.81 | 0.2621 | 0.2758 |
| M7 | 12.11 | 77.32 | 65.21 | 0.2631 | 0.2646 |
| M8 | 13.97 | 81.75 | 67.78 | 0.2677 | 0.2599 |
| M9 | 12.10 | 78.33 | 66.23 | 0.2582 | 0.2560 |
| M10 | 12.81 | 80.89 | 68.08 | 0.2679 | 0.2591 |
| M11 | 12.49 | 73.12 | 60.63 | 0.2486 | 0.2666 |
| M12 | 14.66 | 84.39 | 69.73 | 0.3016 | 0.2868 |
| M13 | 13.44 | 81.71 | 68.27 | 0.2812 | 0.2717 |
| AVERAGE VALUE | — | — | 65.63 | 0.2715 | 0.2715 |
| STANDARD DEVIATION | — | — | — | 0.0175 | 0.0119 |
| COEFFICIENT OF VARIATION (FLUCTUATION DEGREE) | | | | 6.5 | 4.4 |

Fig.33
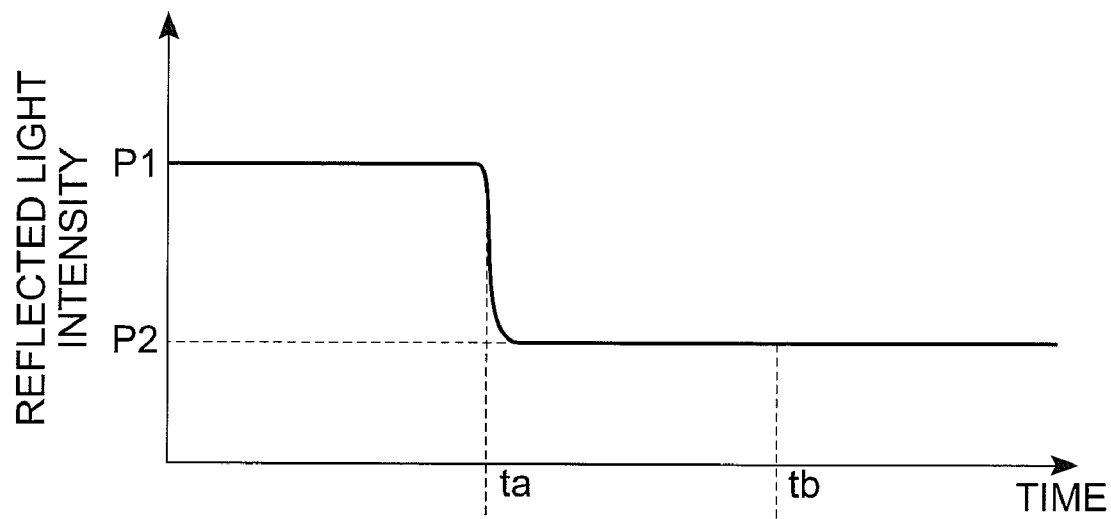
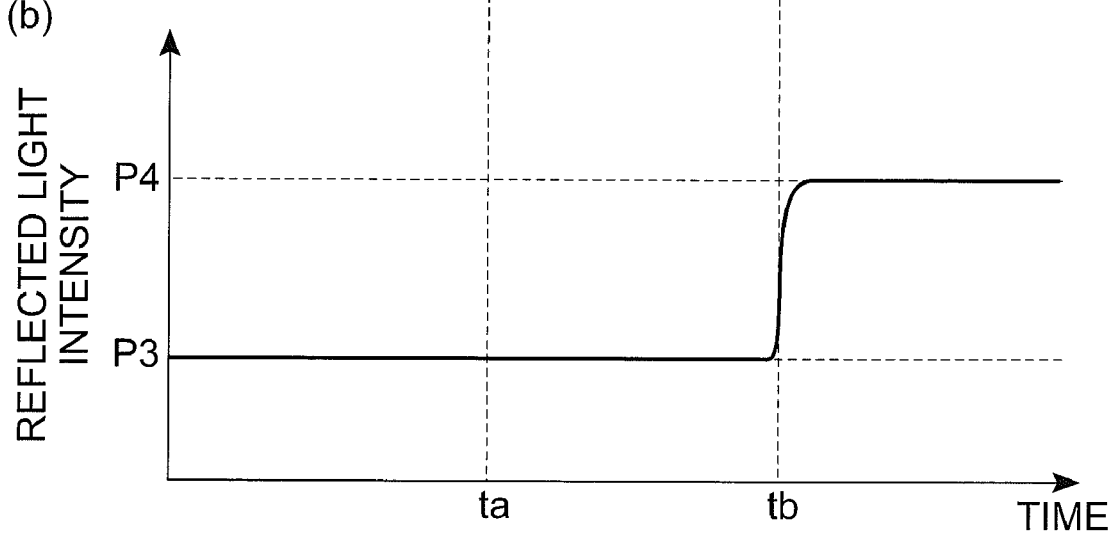

METHOD FOR MEASURING IMMUNOCHROMATO TEST PIECE

TECHNICAL FIELD

The present invention relates to a method for measuring an immunochromatographic test strip.

BACKGROUND ART

On an immunochromatographic test strip, an antibody (or antigen) that causes an antigen-antibody reaction with an antigen (or antibody) in a sample is coated in advance in a band-like manner in a reaction region. When a dye-labeled antigen (or antibody) in the sample is developed to the reaction region of the test strip, the antigen (or antibody) in the sample causes the antigen-antibody reaction with the antibody (or antigen) coated in band-like manner and becomes trapped, and a line colored by the dye is formed in the reaction region. With such an immunochromatographic test strip, by using a measuring apparatus to optically measure a coloration degree (reaction degree) of the line formed in the reaction region, an amount of the antigen (or antibody) in the sample can be analyzed quantitatively.

Each of Patent Documents 1 to 3 discloses an apparatus that illuminates light on an immunochromatographic test strip and detects an intensity of reflected light to measure the coloration degree of the test strip. In the apparatus disclosed in Patent Document 1, the test strip is moved with respect to a measuring system (a light emitting unit and a light receiving unit) that is fixed in position and the reflected light is detected in a continuous manner to measure the coloration degree. The apparatus disclosed in Patent Document 2 has a plurality of light emitting elements and light receiving elements disposed in parallel along a direction in which the sample flows (develops) and measures the coloration degree based on the intensity of the light reflected to the respective light receiving elements. With the apparatus described in Patent Document 3, a change of reflected light intensity is sensed at an arbitrary point on the test strip and measurement is started automatically after a fixed time from the change.

Patent Document 1: Japanese Published Unexamined Patent Application No. Hei 11-83745
Patent Document 2: Japanese Published Unexamined Patent Application No. Hei 10-274624
Patent Document 3: Japanese Published Unexamined Patent Application No. 2003-4743

DISCLOSURE OF THE INVENTION

Problems to be Solved by the Invention

However, there was a problem that fluctuation of reaction degree in the reaction region occurs even when the amount of the antigen (or antibody) in the sample is the same. In order to analyze the amount of the antigen (or antibody) in the sample with good precision, influence due to such fluctuation of reaction degree is preferably suppressed as much as possible.

The present invention has been made in view of the above problem and an object thereof is to provide a method for measuring an immunochromatographic test strip with which influence due to fluctuation of reaction degree is suppressed and which enables an amount of an antigen (or antibody) in a sample to be analyzed with good precision.

Means for Solving the Problems

To achieve the above object, a first method for measuring immunochromatographic test strip according to the present invention is a method in which light obtained from an immunochromatographic test strip by illumination of measurement light is detected to measure a reaction degree of an antigen-antibody reaction and includes the steps of: sensing a change of optical characteristic at a first position on the immunochromatographic test strip by detecting light from the immunochromatographic test strip while illuminating measurement light on the first position after dropping a sample onto the immunochromatographic test strip; sensing a change of optical characteristic at a second position at a downstream side of the first position on the immunochromatographic test strip by detecting light from the immunochromatographic test strip while illuminating measurement light on the second position; and correcting the reaction degree based on an elapsed time from the change of optical characteristic at the first position to the change of optical characteristic at the second position.

The present inventor found that fluctuation of reaction degree in an immunochromatographic test strip is related to fluctuation of flow speed (development speed) of the sample. That is, some factor that causes the fluctuation of reaction degree is manifested as the fluctuation of flow speed (development speed) of the sample. Thus, by measuring the flow speed of the sample and correcting the reaction degree based on the measurement result, influence due to the fluctuation of reaction degree can be suppressed and an amount of the antigen (or antibody) in the sample can be analyzed with good precision.

Because the sample that is developed in the immunochromatographic test strip absorbs light or is developed along with a fluorescent substance, an optical characteristic with respect to the measurement light changes at a position on the immunochromatographic test strip reached by the sample. With the above-described first measuring method, by sensing the change of optical characteristic at the first position on the immunochromatographic test strip by detecting the light from the immunochromatographic test strip while illuminating the measurement light on the first position, and sensing the change of optical characteristic at the second position by detecting the light from the immunochromatographic test strip while illuminating the measurement light on the second position, timings at which the sample reaches the first and second positions respectively can be made known readily. By then correcting the reaction degree based on the elapsed time from the change of optical characteristic at the first position to the change of optical characteristic at the second position (that is, a flow speed of the sample), the influence due to fluctuation of reaction degree can be suppressed and the amount of antigen (or antibody) in the sample can be analyzed with good precision.

A second method for measuring immunochromatographic test strip according to the present invention is a method in which measurement light is illuminated on an immunochromatographic test strip and reflected light is detected to measure a coloration degree of a colored line and includes the steps of: sensing a change of absorbance at a first position on the immunochromatographic test strip by detecting reflected light while illuminating measurement light on the first position after dropping a sample onto the immunochromatographic test strip; sensing a change of absorbance at a second position at a downstream side of the first position on the immunochromatographic test strip by detecting reflected light while illuminating measurement light on the second position; and correcting the coloration degree based on an elapsed time from the change of absorbance at the first position to the change of absorbance at the second position.

Because the sample that is developed in the immunochromatographic test strip absorbs light, the absorbance decreases at a position on the immunochromatographic test strip reached by the sample. With the above-described second measuring method, by sensing the change of absorbance at the first position on the immunochromatographic test strip by detecting the reflected light while illuminating the measurement light on the first position, and sensing the change of absorbance at the second position by detecting the reflected light while illuminating the measurement light on the second position, timings at which the sample reaches the first and second positions respectively can be known readily. By then correcting the coloration degree (reaction degree) based on the elapsed time from the change of absorbance at the first position to the change of absorbance at the second position (that is, a flow speed of the sample), the influence due to fluctuation of coloration degree can be suppressed and the amount of antigen (or antibody) in the sample can be analyzed with good precision.

In the second method for measuring immunochromatographic test strip, the immunochromatographic test strip may have at least one band-like region causing an antigen-antibody reaction with the sample, and the measurement light may be scanned in a sample flow direction so that an illumination position of the measurement light passes through the band-like region after elapse of a predetermined time, longer than the elapsed time, from the change of absorbance at the first position. By thus scanning the band-like region that is to become the colored line and a periphery thereof by the measurement light and detecting the reflected light, the coloration degree can be measured reliably even when an error occurs in the position of the colored line.

Also, in the second method for measuring immunochromatographic test strip, the measurement light may be turned off after the change of absorbance at the second position and then relit thereafter to perform scanning after elapse of the predetermined time. Because an illumination time of the measurement light can thereby be shortened, power consumption can be suppressed and life of a light emitting element, etc., that illuminates the measurement light can be extended.

Preferably in the second method for measuring immunochromatographic test strip, the immunochromatographic test strip has a first band-like region, causing a first antigen-antibody reaction, and a second band-like region, disposed at a downstream side of the first band-like region and causing a second antigen-antibody reaction, and the first position is disposed inside the first band-like region and the second position is disposed inside the second band-like region. The changes of absorbance can thereby be sensed more clearly at the first position and the second position.

Also preferably in the second method for measuring immunochromatographic test strip, measurement of the coloration degree is started after elapse of a predetermined time, longer than the elapsed time, from the change of absorbance at the first position. Because during this predetermined time, the antigen-antibody reaction proceeds, and the colored line is expressed clearly, measurement of the coloration degree can be performed more precisely by this measuring method.

A third method for measuring immunochromatographic test strip according to the present invention includes the steps of illuminating measurement light on a immunochromatographic test strip containing a fluorescent substance after dropping a sample onto the immunochromatographic test strip; and detecting a fluorescence intensity of a reaction line excited by the measurement light to measure a reaction degree of an antigen-antibody reaction at the reaction line; and further includes the steps of: sensing a change of absorbance or a change of fluorescence intensity at a first position on the immunochromatographic test strip by detecting reflected light or fluorescence while illuminating measurement light on the first position after dropping the sample; sensing a change of absorbance or a change of fluorescence intensity at a second position at a downstream side of the first position on the immunochromatographic test strip by detecting reflected light or fluorescence while illuminating measurement light on the second position; and correcting the reaction degree based on an elapsed time from the change of absorbance or fluorescence intensity at the first position to the change of absorbance or fluorescence intensity at the second position.

In the third measuring method, the sample, dropped on the immunochromatographic test strip containing the fluorescent substance, is developed along with the fluorescent substance. Thus, when a position on the immunochromatographic test strip reached by the sample is excited by the measurement light, fluorescence is generated. Because the sample developed in the immunochromatographic test strip also absorbs the measurement light, the absorbance decreases at the position reached by the sample. With the above-described measuring method, by sensing the change of absorbance or the change of fluorescence intensity at the first position on the immunochromatographic test strip by detecting the reflected light or the fluorescence while illuminating the measurement light on the first position, and sensing the change of absorbance or the change of fluorescence intensity at the second position by detecting the reflected light or the fluorescence while illuminating the measurement light on the second position, timings at which the sample reaches the first and second positions respectively can be known readily. By correcting the reaction degree at the reaction line based on the elapsed time from the change of absorbance or fluorescence intensity at the first position to the change of absorbance or fluorescence intensity at the second position (that is, a flow speed of the sample), the influence due to the fluctuation of reaction degree can be suppressed and the amount of antigen (or antibody) in the sample can be analyzed with good precision.

Effect(s) of the Invention

By the method for measuring immunochromatographic test strip according to the present invention, influence due to fluctuation of reaction degree can be suppressed and an amount of antigen (or antibody) in a sample can be analyzed with good precision.

BRIEF DESCRIPTION OF THE DRAWINGS

FIG. 13 shows (a) a schematic graph showing a manner of change of absorbance at a first position, and (b) a schematic graph showing a manner of change of absorbance at a second position.

FIG. 15 is a table of results of an example.

FIG. 33 shows (a) a schematic graph showing a manner of change of absorbance at the first position, and (b) a schematic graph showing a manner of change of fluorescence intensity at the second position.

DESCRIPTION OF SYMBOLS 1a-1e . . . Measuring apparatus, 2, 3, 5-9 . . . Optical head, 11 . . . Setting plate, 12 . . . Drive mechanism, 13, 14 . . . Controller, 21, 31, 51, 61, 71, 72, 81, 91 . . . Light emitting element, 22, 32, 52, 62, 73, 74, 82, 92 Photodetecting element, 23a . . . Aperture, 24a, 33a . . . Slit, 25 . . . Resin member, 26 . . . PC substrate, 34 . . . Lens, 41 . . . Immunochromatographic test strip, 41c, 41d . . . Band-like region, 42 . . . Immunochromatographic test utensil, CL . . . Control line, TL . . . Test line.

BEST MODES FOR CARRYING OUT THE INVENTION

Embodiments of a method for measuring immunochromatographic test strip according to the present invention shall now be described in detail with reference to the attached drawings. In the description of the drawings, elements that are the same are provided with the same symbol and redundant description is omitted.

First Embodiment

Figure 1:
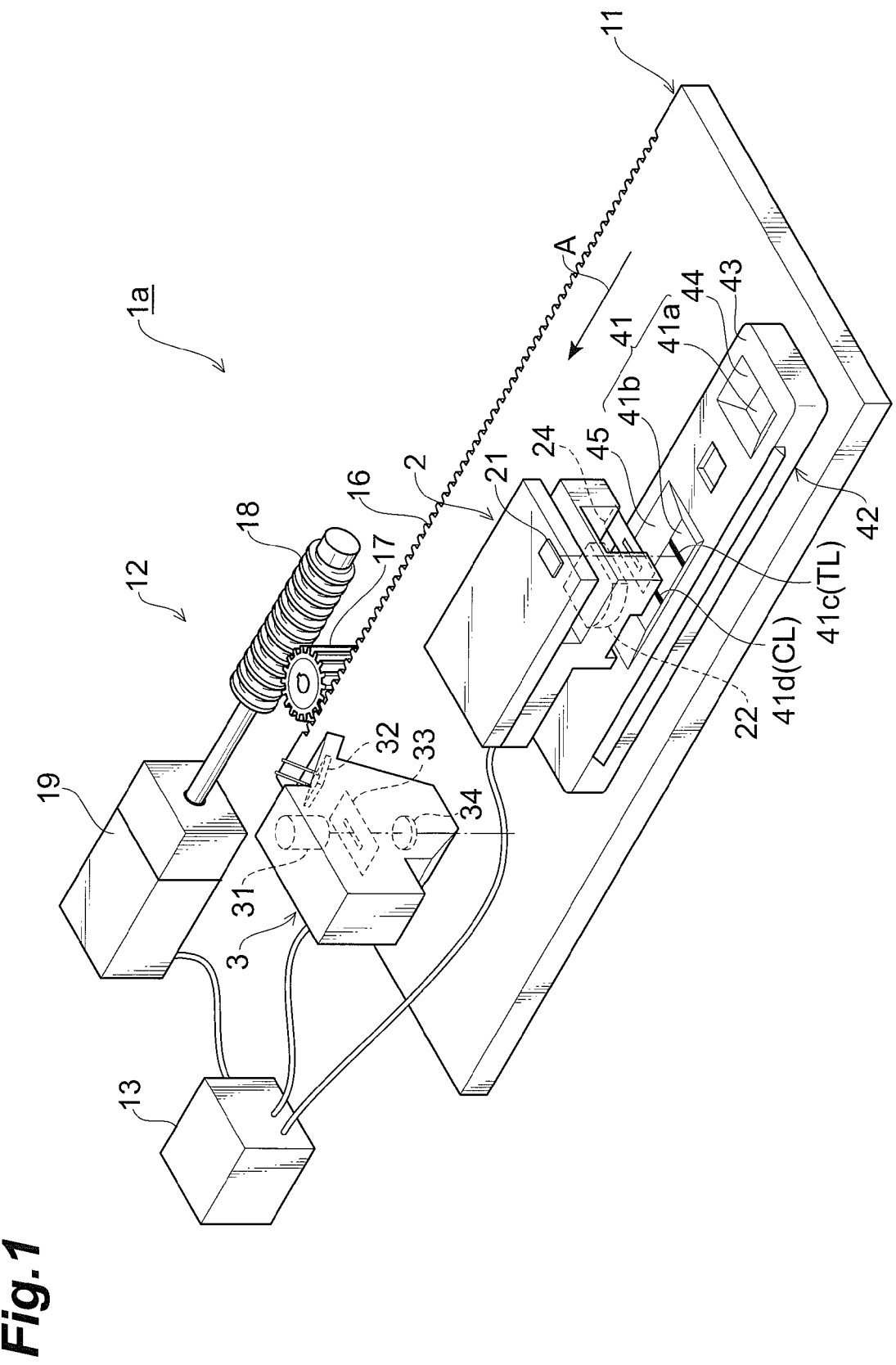
FIG. 1 is a perspective view of a configuration of a measuring apparatus used favorably in a method for measuring immunochromatographic test strip according to a first embodiment.

Before describing a method for measuring immunochromatographic test strip according to the present embodiment, a measuring apparatus having a configuration favorable for carrying out the present measuring method shall be described. FIG. 1 is a perspective view of the configuration of the measuring apparatus 1a used favorably in the measuring method according to the present embodiment. The measuring apparatus 1a illuminates measurement light on a test line TL and a control line CL, which are colored lines (reaction lines) formed on an immunochromatographic test strip 41, and detects intensities of reflected light of the measurement light to measure coloration degrees (reaction degrees) of the colored lines TL and CL. As shown in FIG. 1, the measuring apparatus 1a includes: a setting plate (test strip support) 11, for supporting an immunochromatographic test utensil 42 that has the immunochromatographic test strip 41; an optical head 2, integrally incorporating a light emitting element 21, which is a light illuminating unit that illuminates the measurement light on the immunochromatographic test strip 41, and a photodetecting element 22, which is a photodetecting unit that detects the reflected light from the immunochromatographic test strip 41; an optical head 3, integrally incorporating a light emitting element 31, which is a light illuminating unit that illuminates the measurement light on the immunochromatographic test strip 41, and a photodetecting element 32, which is a photodetecting unit that detects the reflected light from the immunochromatographic test strip 41; a drive mechanism 12, moving the setting plate 11 in a sample flow direction (arrow A in the figure) relative to the optical heads 2 and 3; and a controller 13, controlling the optical heads 2 and 3 and the drive mechanism 12.

Figure 2:
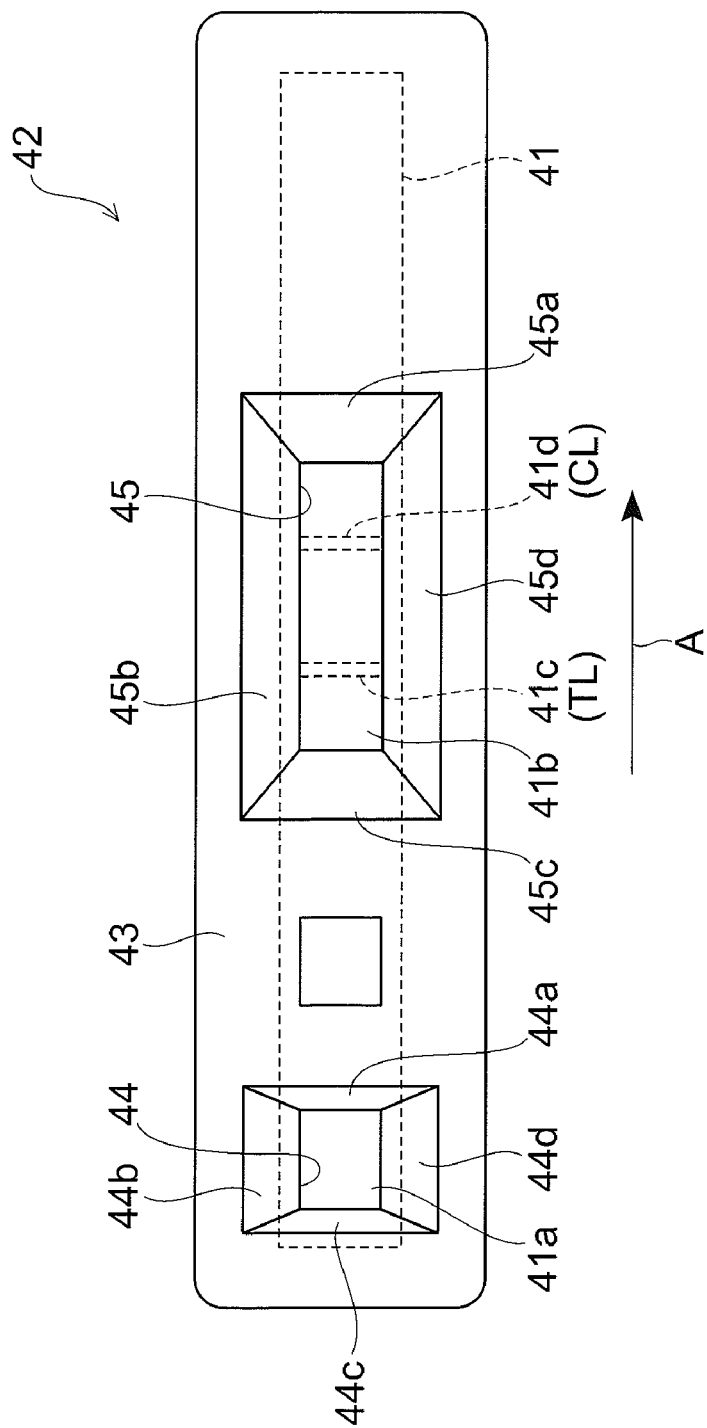
FIG. 2 is a plan view of an immunochromatographic test utensil.

FIG. 2 is a plan view of the immunochromatographic test utensil 42. As shown in FIG. 2, the immunochromatographic test utensil 42 includes a casing 43 with a rectangular shape in plan view, and the immunochromatographic test strip 41 held inside the casing 43.

Along a direction of its long side, the casing 43 has a sample application window 44 for dropping a sample, and an observation window 45 that exposes colored portions of the immunochromatographic test strip 41. Edges 44a to 44d forming the sample application window 44 and edges 45a to 45d forming the observation window 45 have tapered shapes inclining toward the immunochromatographic test strip 41.

The immunochromatographic test strip 41 is made of a material, such as nitrocellulose membrane, filter paper, etc., and has a rectangular shape. The immunochromatographic test strip 41 includes a sample application portion 41a, disposed at a position corresponding to the sample application window 44, and a detection portion 41b, disposed at a position corresponding to the observation window 45. The detection portion 41b includes a first band-like region 41c, extending in a direction intersecting the sample flow direction (arrow A in the figure), which is a longitudinal direction of the immunochromatographic test strip 41, and a second band-like region 41d, disposed parallel and at a downstream side in the sample flow direction A with respect to the band-like region 41c. An antibody (or antigen), causing a first antigen-antibody reaction with an antigen (or antibody) in the sample, is coated and fixed in a line-like (band-like) manner in the band-like region 41c, and an antibody (or antigen), causing a second antigen-antibody reaction with a dye-labeled antibody (or antigen) (hereinafter, "reference dye") that binds with the antigen (or antibody) in the sample, is coated and fixed in a line-like (band-like) manner in the band-like region 41d. In the band-like region 41d, instead of the abovementioned reference dye, an antibody (or antigen), causing a second antigen-antibody reaction with a dye-labeled antibody (or antigen) that does not bind with the antigen (or antibody) in the sample, may be coated and fixed in a line-like (band-like) manner.

The sample is dropped onto the sample application portion 41a of the immunochromatographic test strip 41 from the sample application window 44. An antigen (or antibody) in the sample binds with a label dye, and a complex of the antigen (or antibody) in the sample and the label dye and unreacted label dye move in the direction of the long side of the immunochromatographic test strip 41. It shall now be supposed that an antigen is contained in the sample and the antigen undergoes the antigen-antibody reaction at the band-like region 41c. In accordance with the movement of the sample, the antigen in the sample and an antibody fixed to the band-like region 41c react specifically, and a colored line (test line TL) is formed by the label dye at the reacted band-like region 41c. Meanwhile, the unreacted label dye reacts specifically with an antibody fixed to the band-like region 41d, and a colored line (control line CL) is formed by the label dye at the reacted band-like region 41d. The colored lines TL and CL normally have a width of approximately 1.0 mm. The colored lines TL and CL normally have a length in a longitudinal direction of approximately 5 mm.

Figure 3:
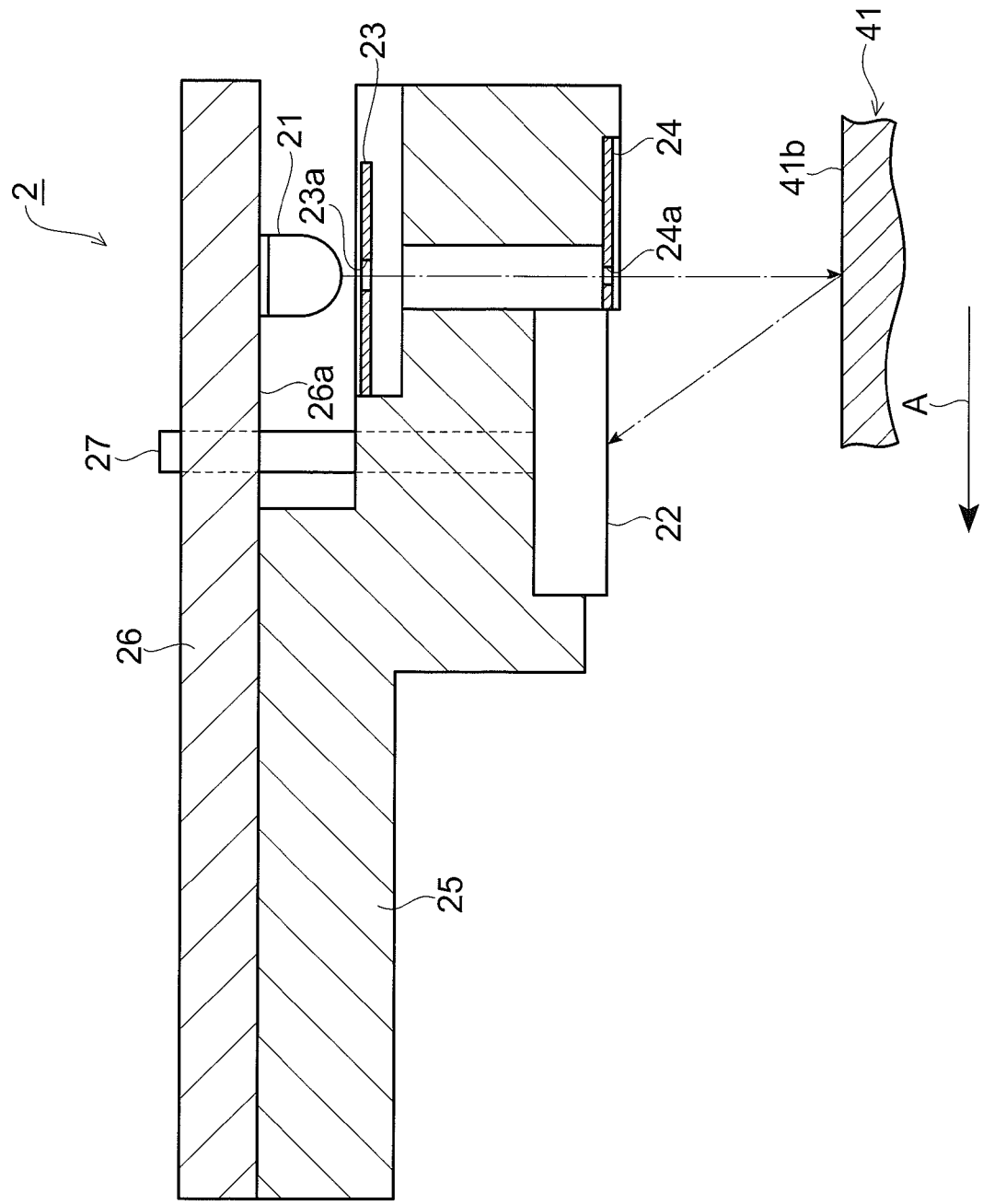
FIG. 3 is a side sectional view of an optical head taken along a movement direction of a sample.
Figure 4:
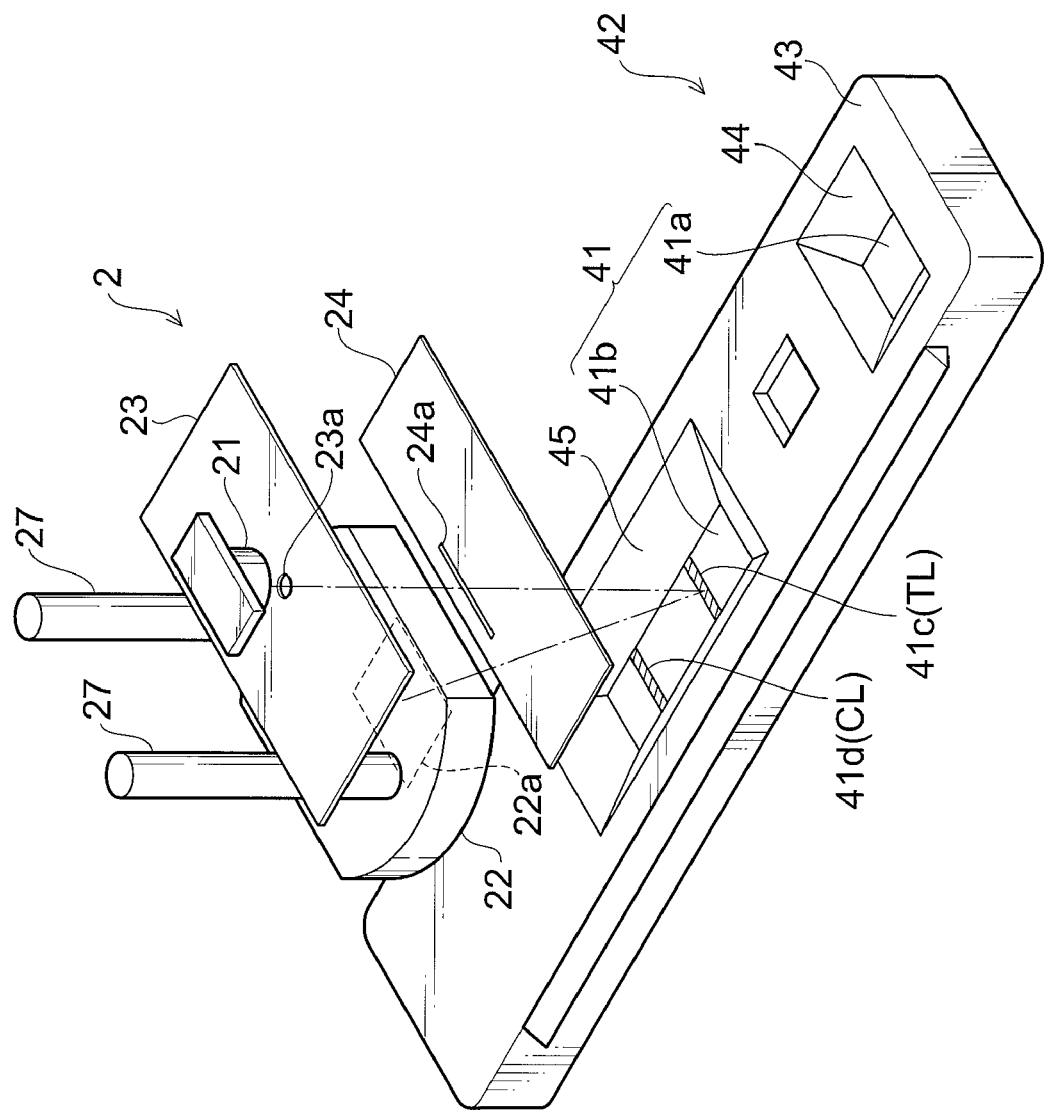
FIG. 4 is a perspective view of the optical head and the immunochromatographic test utensil.

FIG. 3 is a side sectional view of the optical head 2 taken along the movement direction of the sample. FIG. 4 is a perspective view of the optical head 2 and the immunochromatographic test utensil 42. To facilitate understanding, a resin member 25 and a PC substrate 26 that the optical head 2 has are omitted from illustration in FIG. 4.

As shown in FIGS. 3 and 4, the optical head 2 includes the light emitting element 21, the photodetecting element 22, beam shaping members 23 and 24, the resin member 25 (FIG. 3), and the PC substrate 26 (FIG. 3). In the present embodiment, a semiconductor light emitting element, such as a light emitting diode (LED), is used as the light emitting element 21, and a semiconductor photodetecting element, such as a silicon (Si) photodiode, is used as the photodetecting element 22. The light emitting element 21 is mounted on a rear surface 26a of the PC substrate 26 so that an optical axis thereof is perpendicular to a top surface of the immunochromatographic test strip 41 and illuminates the measurement light on the immunochromatographic test strip 41. The photodetecting element 22 is mounted on the PC substrate 26 via two metal rods 27 joined to the photodetecting element 22, receives the reflected light from the immunochromatographic test strip 41 on a photodetection surface 22a, and converts the reflected light to an electrical signal that is in accordance with the intensity of the reflected light. The photodetecting element 22 in the present embodiment is disposed at a downstream side in the sample flow direction A with respect to the optical axis of the light emitting element 21.

The beam shaping members 23 and 24 are members for shaping the light from the light emitting element 21 to light having a beam cross section that extends in a direction substantially parallel to the band-like regions 41c and 41d of the immunochromatographic test strip 41 (see FIG. 2) and are disposed in parallel along an optical axis direction (direction perpendicular to the top surface of the immunochromatographic test strip 41) of the light emitting element 21. The beam shaping member 23 is made of a plate-like member having an aperture 23a of substantially circular shape formed therein. The beam shaping member 24 is made of a plate-like member having formed therein a slit 24a that extends substantially parallel to the band-like regions 41c and 41d. As shown in FIG. 3, the photodetecting element 22 and the beam shaping members 23 and 24 are held integrally by the block-like resin member 25 joined to the rear surface 26a of the PC substrate 26 and are thereby defined in mutual positional relationship.

Figure 5:
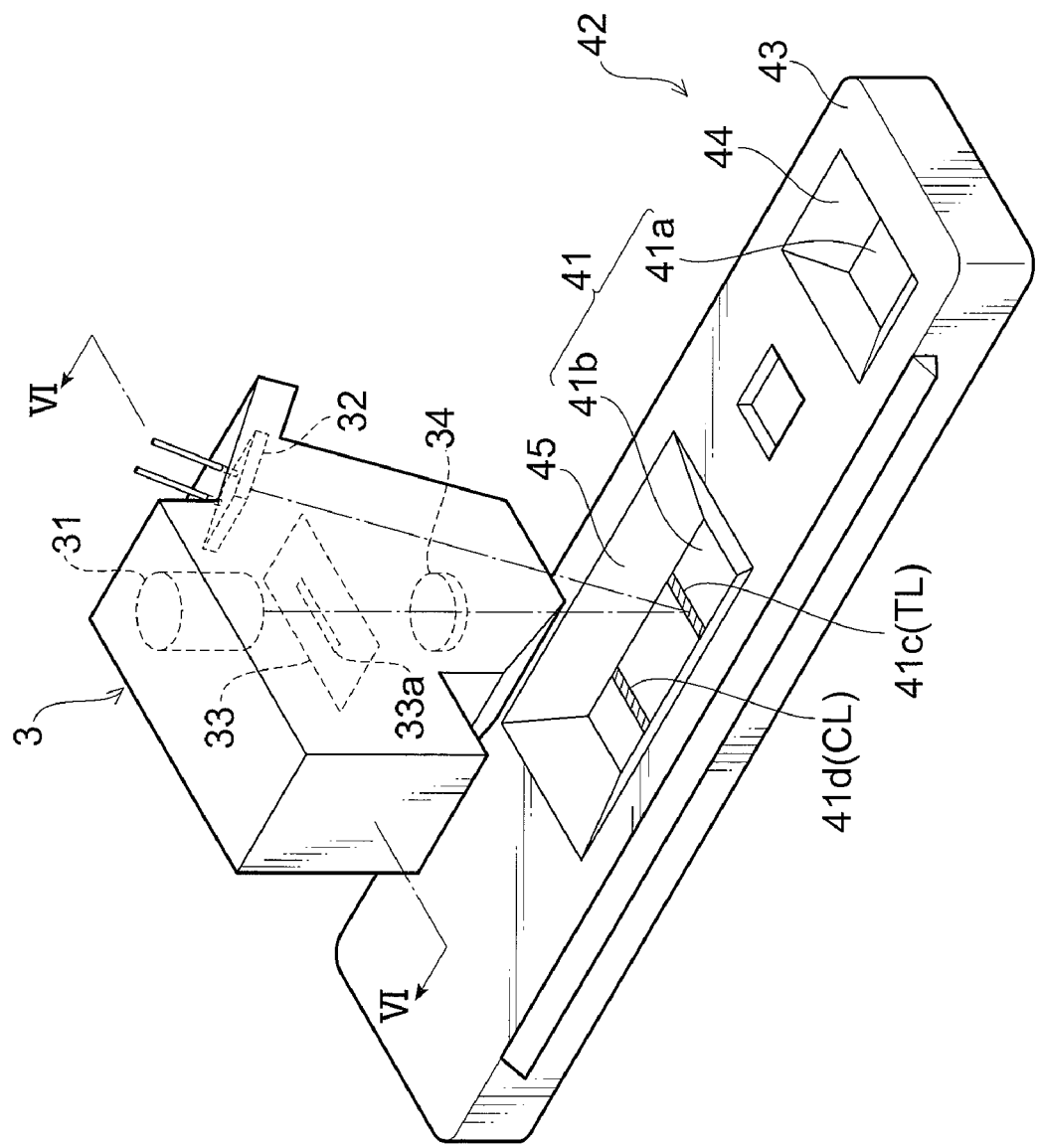
FIG. 5 is a perspective view of the optical head and the immunochromatographic test utensil.
Figure 6:
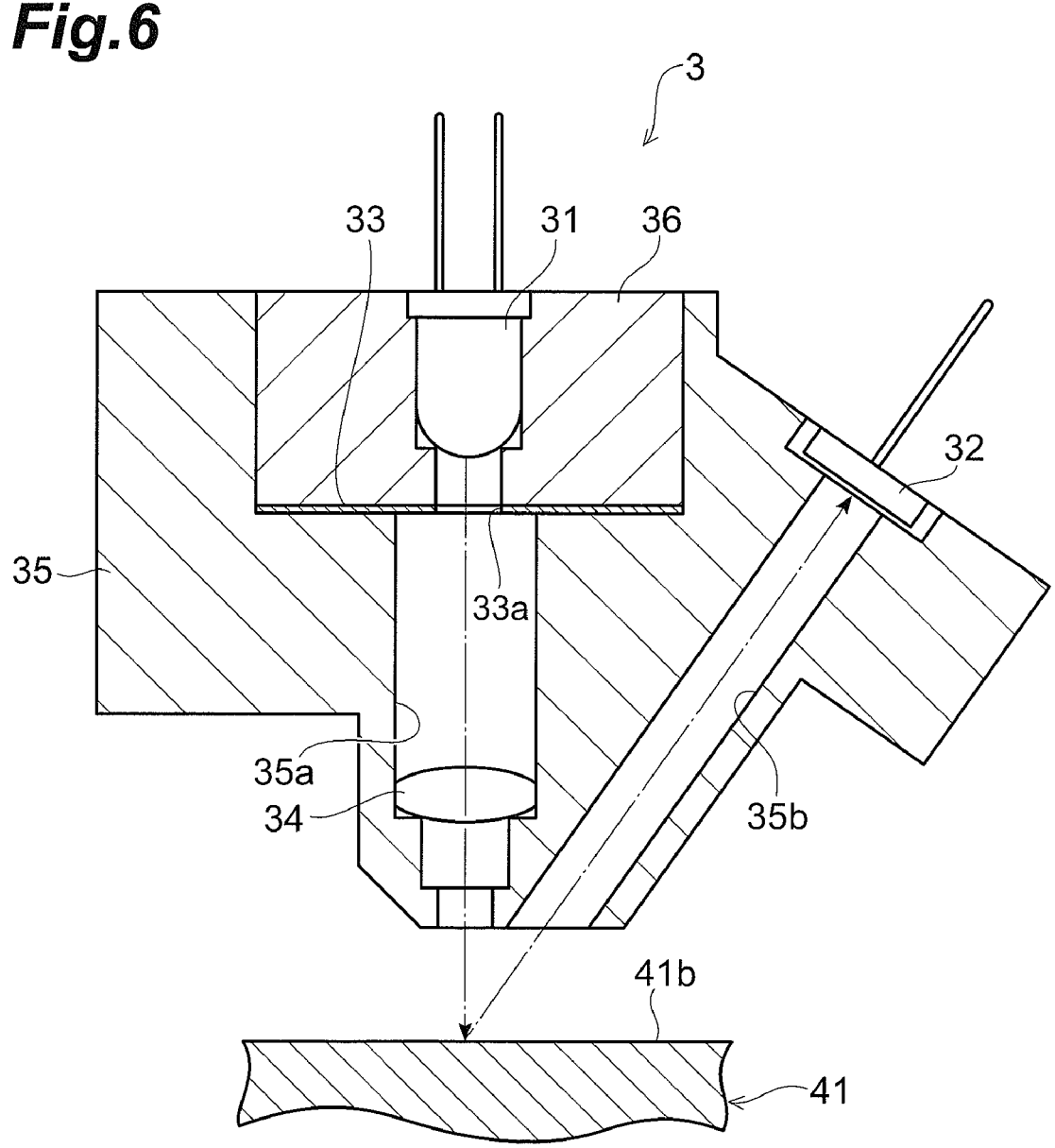
FIG. 6 is a sectional view taken on section VI-VI of the optical head shown in FIG. 5.

FIG. 5 is a perspective view of the optical head 3 and the immunochromatographic test utensil 42. FIG. 6 is a sectional view taken on section VI-VI of the optical head 3 shown in FIG. 5.

The optical head 3 includes the light emitting element 31, the photodetecting element 32, a beam shaping member 33, and a lens 34, and these are held integrally and defined in mutual positional relationship by members 35 and 36. In the present embodiment, a semiconductor light emitting element, such as a light emitting diode (LED), is used as the light emitting element 31, and a semiconductor photodetecting element, such as a silicon (Si) photodiode, is used as the photodetecting element 32. The light emitting element 31 is held by the member 36 so that an optical axis thereof is perpendicular to the top surface of the immunochromatographic test strip 41 and illuminates the measurement light on the immunochromatographic test strip 41. The photodetecting element 32 is disposed obliquely upward in a direction substantially parallel to the band-like regions 41c and 41d (see FIG. 2) from an illumination position of the measurement light on the immunochromatographic test strip 41 and converts reflected light from the immunochromatographic test strip 41 to an electrical signal that is in accordance with the intensity of the reflected light.

The beam shaping member 33 is a member for shaping the light from the light emitting element 31 to light having a beam cross section extending in a direction substantially parallel to the band-like regions 41c and 41d of the immunochromatographic test strip 41 (see FIG. 2). The beam shaping member 33 is made of a plate-like member having formed therein a slit 33a that extends substantially parallel to the band-like regions 41c and 41d. As shown in FIG. 6, the beam shaping member 33 is sandwiched and fixed between the member 35 and the member 36, which is fitted in a recess of the member 35 and holds the light emitting element 31. The lens 34 is for image forming of light from the beam shaping member 33 (slit light substantially parallel to the band-like regions 41c and 41d) on the immunochromatographic test strip 41. The lens 34 is disposed along an optical axis of the measurement light emitted from the light emitting element 31 and is held by the member 35.

The member 35 holds the photodetecting element 32 and the lens 34. In the member 35 are formed a hole 35a, surrounding an optical path of the measurement light emitted from the light emitting element 31, and a hole 35b, surrounding an optical path of light reflected from the immunochromatographic test strip 41 and made incident on the photodetecting element 32. At one end of the hole 35*a*, the light emitting element 31, held by the member 36, is disposed via the slit 33*a*, and the other end of the hole 35*a* opposes the illumination position of the light of the immunochromatographic test strip 41. The lens 34 is held inside the hole 35*a*. At one end of the hole 35*b*, the photodetecting element 32 is disposed, and the other end of the hole 35*b* opposes the illumination position of the light of the immunochromatographic test strip 41. In this configuration, the holes 35*a* and 35*b* function as baffles that prevent the measurement light, emitted from the light emitting element 31, from leaking to an exterior of the optical head 3 and noise light (stray light) besides the reflected light from becoming incident on the photodetecting element 32.

FIG. 1 is referred to again. The drive mechanism 12 is for moving the setting plate 11 along the sample flow direction A with respect to the optical heads 2 and 3. The drive mechanism 12 includes a pinion 17, engaging with a rack 16 formed on a side surface of the setting plate 11 along the sample flow direction A, a drive motor 19, to which is fixed a worm gear 18 that engages with the pinion 17, etc. With the drive mechanism 12, when the worm gear 18 is rotated in a forward rotation direction by the drive motor 19, the pinion 17 is driven to rotate in a speed-reduced manner, and the setting plate 11, with which the rack 16 engages with the pinion 17, moves in a direction opposite the sample flow direction A. Consequently, the optical heads 2 and 3 are moved in a relative manner with respect to the setting plate 11 in the sample flow direction A.

The controller 13 is provided for rotation control of the drive motor 19, lighting control of the light emitting elements 21 and 31, and processing of output signals from the photodetecting elements 22 and 32.

Figure 7:
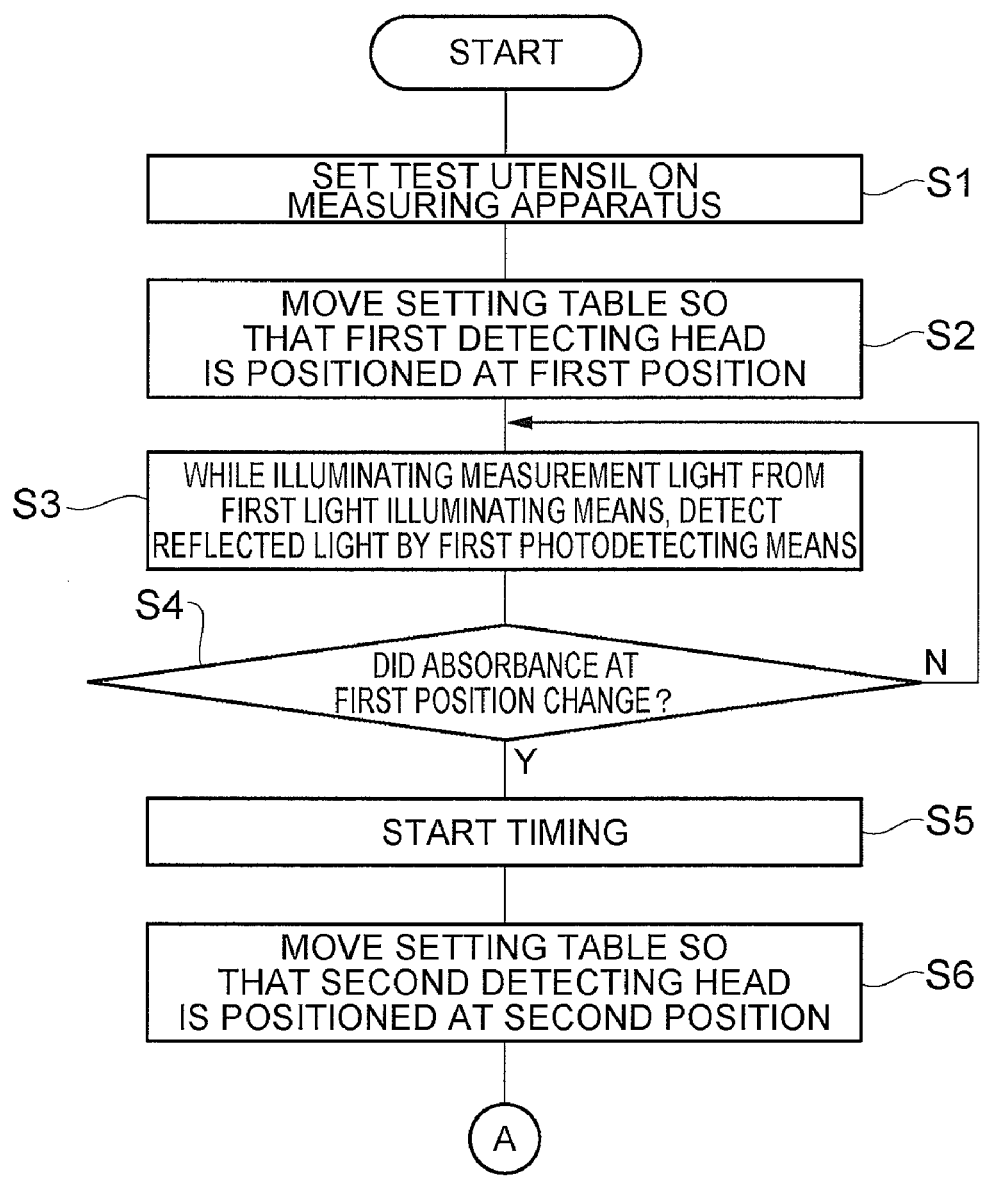
FIG. 7 is a flowchart of the measuring method according to the first embodiment.
Figure 8:
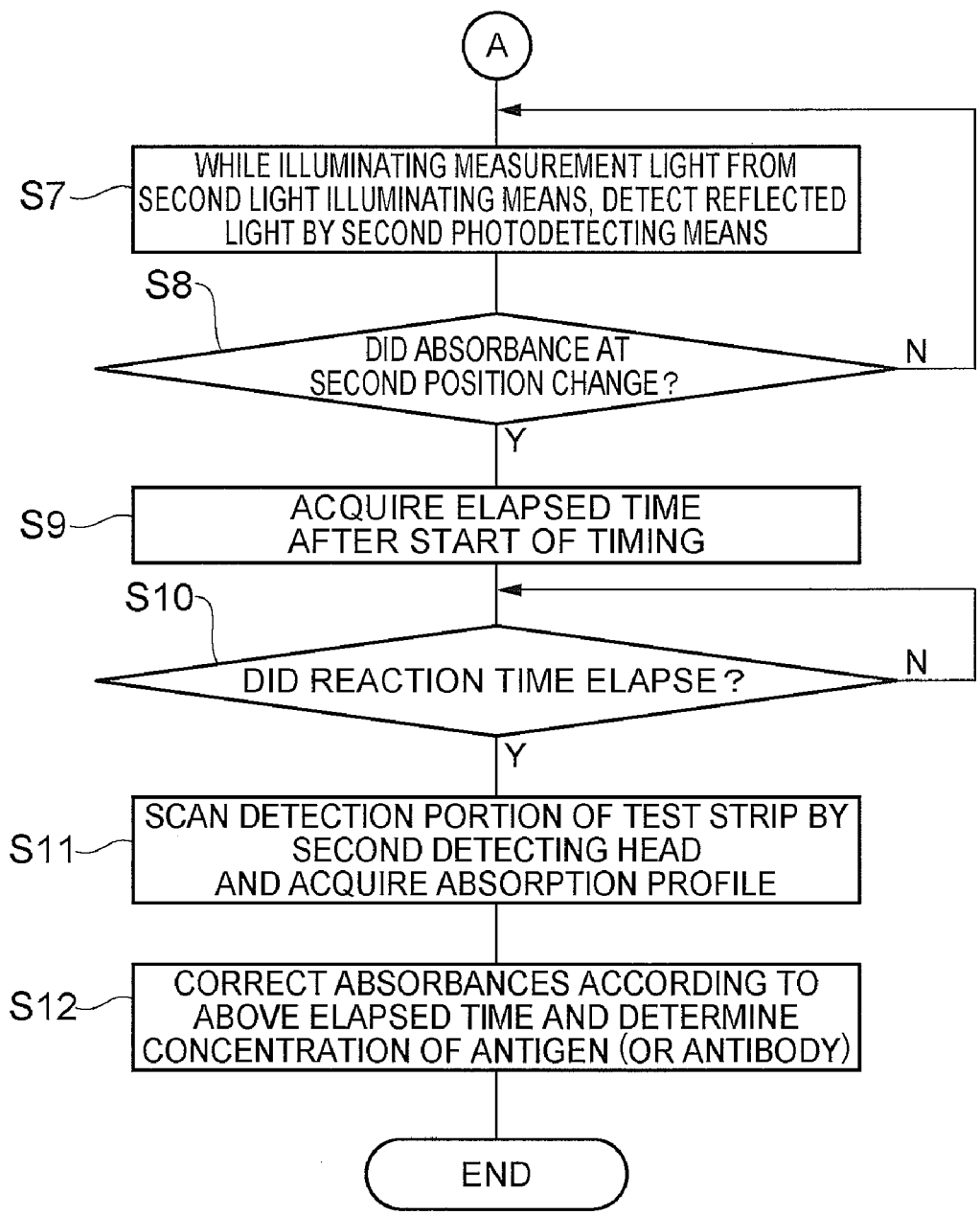
FIG. 8 is a flowchart of the measuring method according to the first embodiment.

The method for measuring immunochromatographic test strip according to the present embodiment shall now be described with reference to FIGS. 7 to 12. FIGS. 7 and 8 are flowcharts of the measuring method according to the present embodiment. FIGS. 9 to 12 are perspective views for describing operating states of the measuring apparatus 1*a*. In FIGS. 9 to 12, the drive mechanism 12 and the controller 13 shown in FIG. 1 are omitted from illustration.

Figure 9:
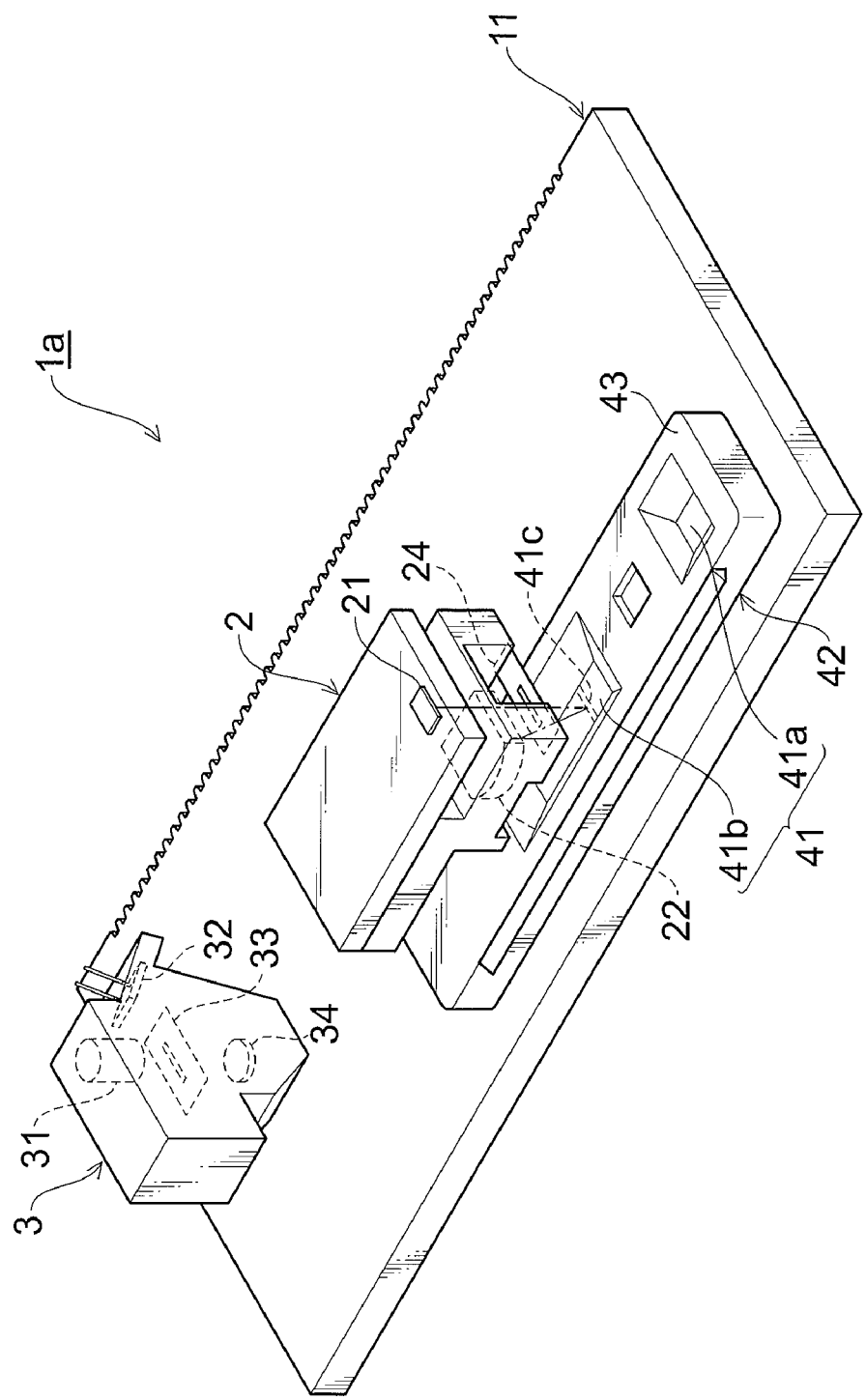
FIG. 9 is a perspective view for describing an operating state of the measuring apparatus of the first embodiment.

First, a measurer sets the immunochromatographic test utensil 42 on the setting plate 11 (step S1). The controller 13 then moves the setting plate 11 and the optical head 2 in a relative manner so as to detect the reflected light from a first position on the immunochromatographic test strip 41 determined in advance. Specifically, the controller 13 moves the setting plate 11 by actuating the drive mechanism 12 and thereby controls the relative positional relationship of the optical head 2 and the immunochromatographic test strip 41 so that the first position on the immunochromatographic test strip 41 is positioned in a light emitting direction of the light emitting element 21 of the optical head 2 (specifically, a direction in which light that has passed through the aperture 23*a* and the slit 24*a* propagates) (step S2). In the present embodiment, the first position on the immunochromatographic test strip 41 is set inside the first band-like region 41*c*. Thus, as shown in FIG. 9, the band-like region 41*c* is positioned in the light emitting direction of the light emitting element 21.

Next, after the measurer drops a sample onto the sample application portion 41*a*, the light emitting element 21 illuminates the measurement light on the first position (that is, the band-like region 41*c*) of the immunochromatographic test strip 41. The photodetecting element 22 receives the reflected light and converts it to an electrical signal that is in accordance with the light intensity. The electrical signal is transmitted to the controller 13, and based on this electrical signal, the controller 13 senses the reflected light intensity at the first position (band-like region 41*c*) (step S3). The light emitting element 31 is unlit at this point.

FIG. 13(*a*) is a schematic graph showing a manner of change of an optical characteristic (absorbance) at the first position (band-like region 41*c*). In FIG. 13(*a*), an ordinate indicates the reflected light intensity at the first position (band-like region 41*c*) and an abscissa indicates time. Normally, in a dry state, the immunochromatographic test strip 41 is low in absorbance and reflected light of a comparatively high intensity P1 is detected by the photodetecting element 22. When the sample reaches the first position (band-like region 41*c*), because the sample absorbs a portion of the measurement light and the absorbance at the first position (band-like region 41*c*) increases, the intensity of the light reflected to the photodetecting element 22 changes to an intensity P2 that is lower than the intensity P1. The controller 13 observes the change of absorbance based on the electrical signal from the photodetecting element 22 (step S4) and starts timing at a time to at which the absorbance changed (step S5). After sensing the change of absorbance at the first position (band-like region 41*c*), the controller 13 turns off the light emitting element 21.

Figure 10:
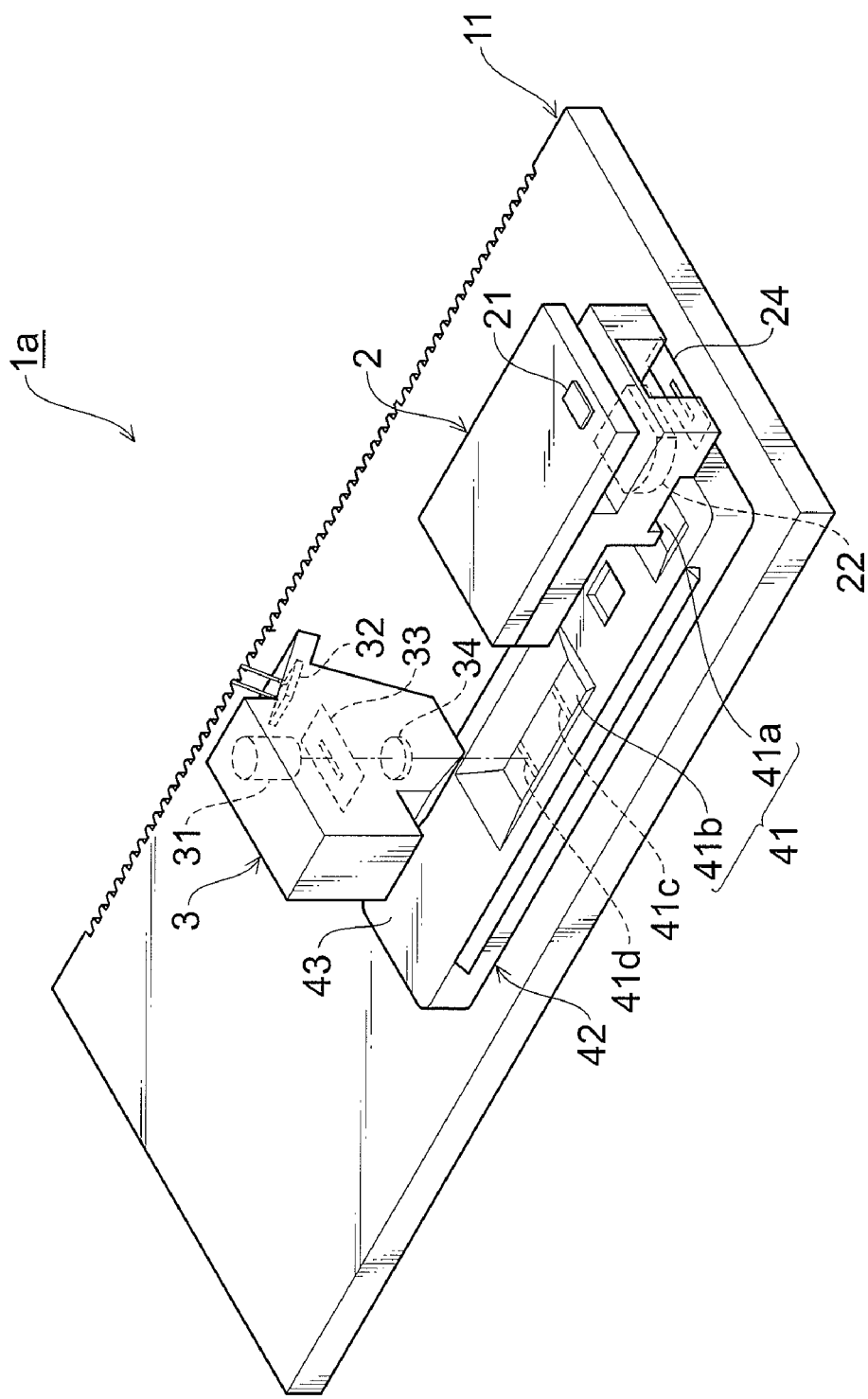
FIG. 10 is a perspective view for describing an operating state of the measuring apparatus of the first embodiment.

Subsequently, the controller 13 moves the setting plate 11 and the optical head 3 in a relative manner so as to detect reflected light from a second position on the immunochromatographic test strip 41 at a downstream side of the first position. Specifically, the controller 13 moves the setting plate 11 by actuating the drive mechanism 12 again and thereby controls the relative positional relationship of the optical head 3 and the immunochromatographic test strip 41 so that the second position on the immunochromatographic test strip 41 is positioned in a light emitting direction of the light emitting element 31 of the optical head 3 (specifically, a direction in which light that has passed through the slit 33*a* and the lens 34 propagates) (step S6). In the present embodiment, the second position on the immunochromatographic test strip 41 is set inside the second band-like region 41*d*. Thus, as shown in FIG. 10, the band-like region 41*d* is positioned in the light emitting direction of the light emitting element 31. Thereafter, the controller 13 lights the light emitting element 31, and the light emitting element 31 illuminates the measurement light on the second position (that is, the band-like region 41*d*) of the immunochromatographic test strip 41. The photodetecting element 32 receives the reflected light and converts it to an electrical signal that is in accordance with the light intensity. The electrical signal is transmitted to the controller 13, and based on this electrical signal, the controller 13 senses the reflected light intensity at the second position (band-like region 41*d*) (step S7).

FIG. 13(*b*) is a schematic graph showing a manner of change of an optical characteristic (absorbance) at the second position (band-like region 41*d*). In FIG. 13(*b*), the ordinate indicates the reflected light intensity at the second position (band-like region 41*d*) and the abscissa indicates time. As mentioned above, until the sample reaches the second position (band-like region 41*d*), reflected light of a comparatively high intensity P1 is detected by the photodetecting element 32. When the sample reaches the second position (band-like region 41*d*), because the absorbance at the second position (band-like region 41*d*) increases, the intensity of the light reflected to the photodetecting element 32 changes to an intensity P2 (<P1). The controller 13 observes the change of absorbance based on the electrical signal from the photodetecting element 32 (step S8) and acquires a difference between a time tb at which the absorbance changed and the time ta (tb−ta), that is, an elapsed time from the change of absorbance at the first position (band-like region 41c) to the change of absorbance at the second position (band-like region 41d) (step S9). After the absorbance at the second position (band-like region 41d) has changed, the controller 13 turns off the light emitting element 31 once.

Then, using the time ta as a reference, the controller 13 performs counting of a predetermined time (step S10). During this predetermined time, the abovementioned first and second antigen-antibody reactions proceed so that the band-like regions 41c and 41d become colored and the colored lines TL and CL become expressed. This predetermined time is set longer than the abovementioned elapsed time (tb−ta), for example, to approximately 15 minutes and adjusted as suited according to the type of the sample.

Figure 11:
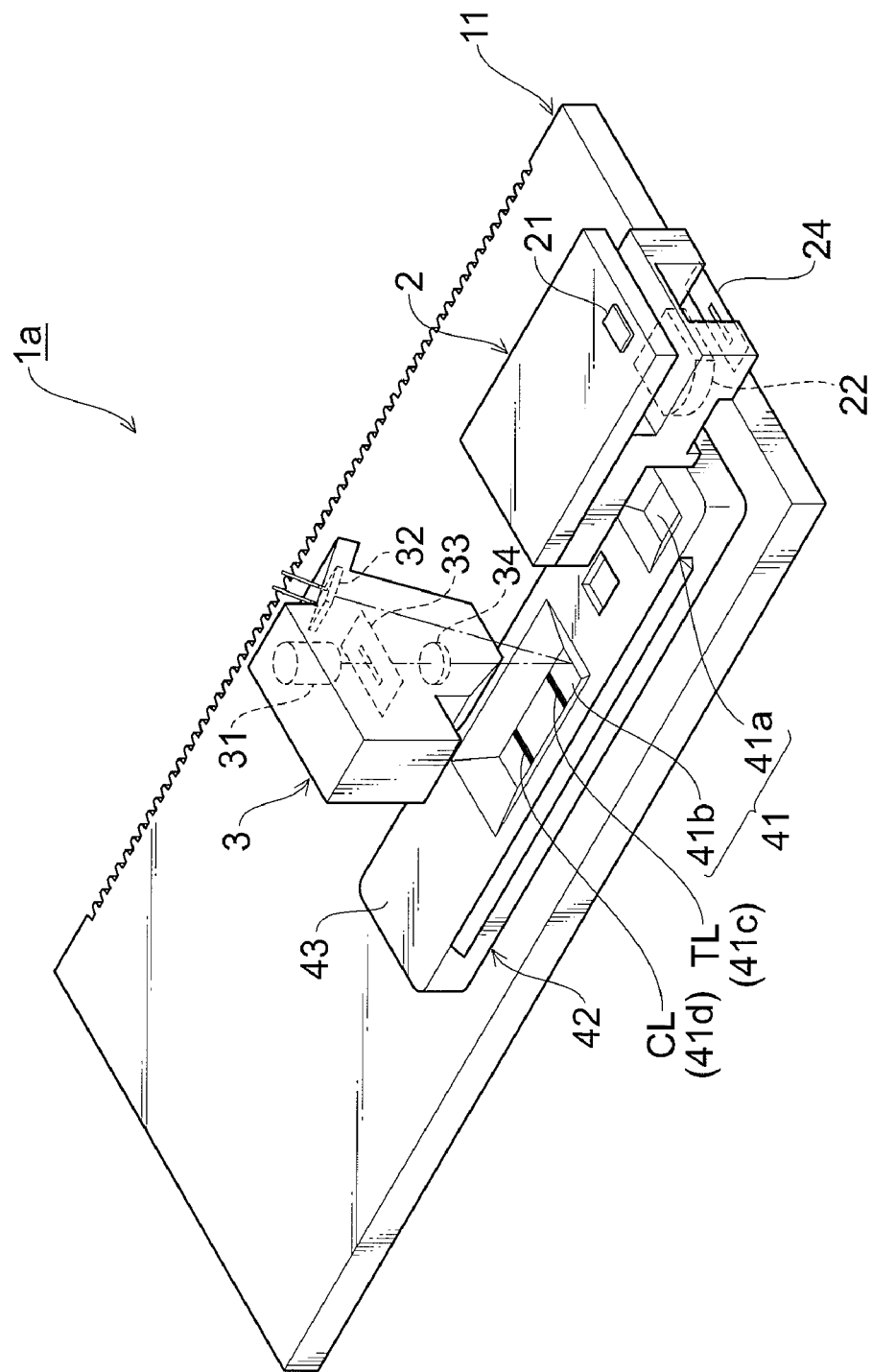
FIG. 11 is a perspective view for describing an operating state of the measuring apparatus of the first embodiment.
Figure 12:
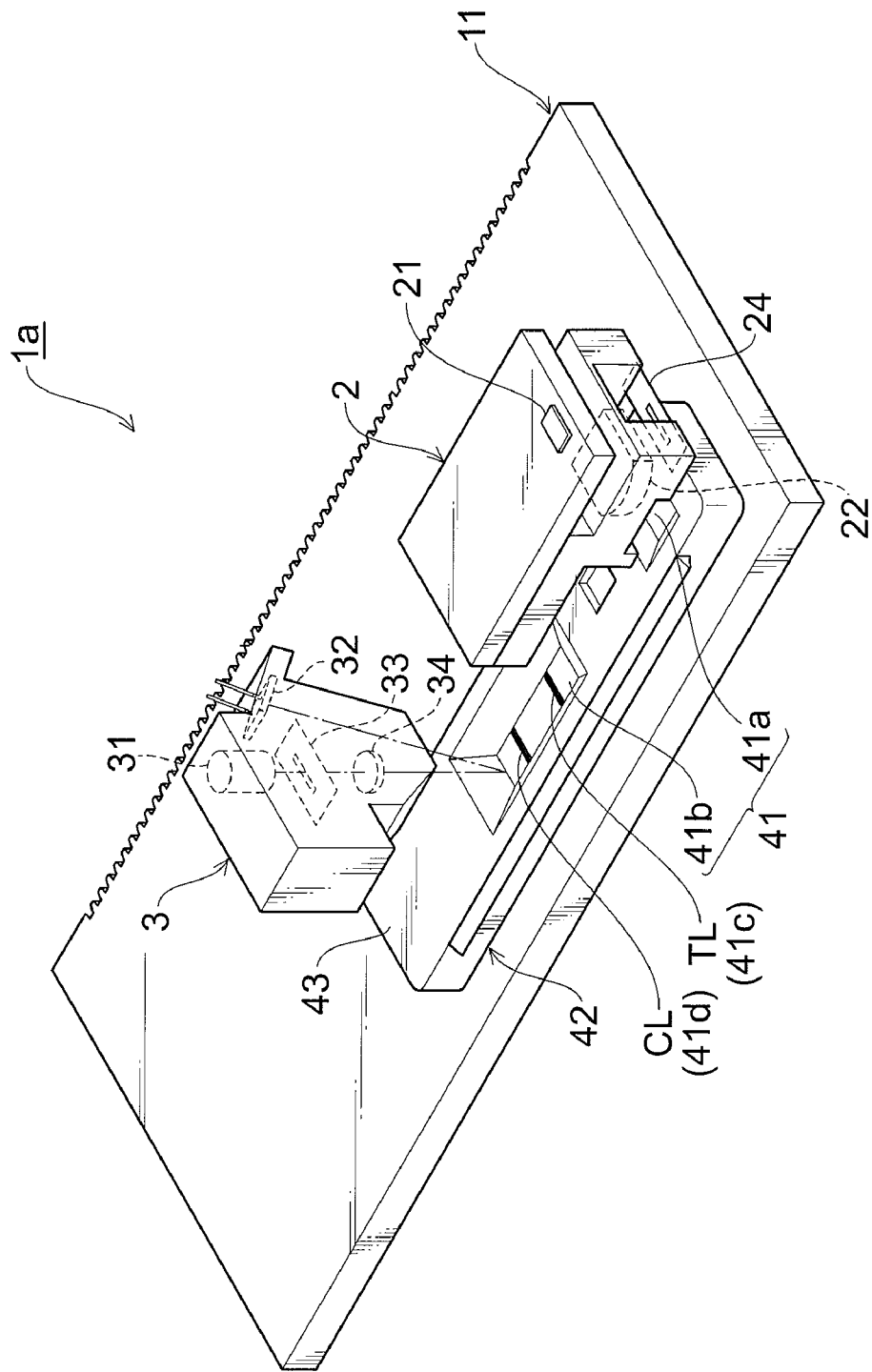
FIG. 12 is a perspective view for describing an operating state of the measuring apparatus of the first embodiment.

After the elapse of the predetermined time, the controller 13 relights the light emitting element 31, and while scanning the measurement light of the light emitting element 31 in the sample flow direction so that the illumination position of the measurement light passes through the band-like regions 41c and 41d, detects the reflected light by the photodetecting element 32 continuously (or intermittently), and obtains an absorbance profile of the measurement light in the detection portion 41b (step S11). Specifically, the controller 13 actuates the drive mechanism 12 again to move the setting plate 11 and makes an end at the upstream side of the detection portion 41b be positioned in the light emitting direction of the light emitting element 31 as shown in FIG. 11. Then, while moving the illumination position of the measurement light toward the downstream side (that is, while moving the immunochromatographic test strip 41 toward the upstream side relative to the optical head 3) until an end at the downstream side of the detection portion 41b is positioned in the light emitting direction of the light emitting element 31 (see FIG. 12), the controller 13 makes the light emitting element 31 illuminate the measurement light and acquires the electrical signal that is in accordance with the reflected light intensity by the photodetecting element 32.

Figure 14:
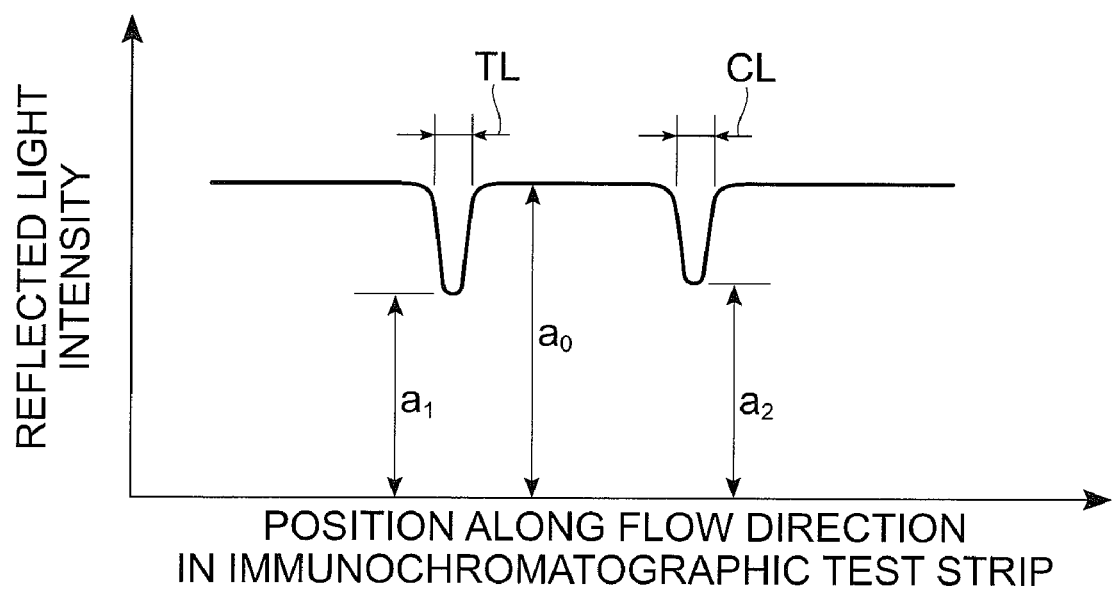
FIG. 14 is a diagram of an example of an absorbance profile of measurement light.

FIG. 14 is a diagram of an example of an absorbance profile of measurement light obtained by the above-described operation. In FIG. 14, the ordinate indicates the reflected light intensity and the abscissa indicates the position on the detection portion 41b in the sample flow direction. The controller 13 prepares the absorbance profile such as that shown in FIG. 14, and from the absorbance profile, computes an absorbance $ABS_1$ of the test line TL and an absorbance $ABS_2$ of the control line CL on the immunochromatographic test strip by the computation formulae: $ABS_1=\log(a_1/a_0)$; and $ABS_2=\log(a_2/a_0)$; respectively. The absorbances $ABS_1$ and $ABS_2$ express the respective coloration degrees of the colored lines TL and CL. Based on a relationship formula set in advance, the controller 13 corrects the absorbances $ABS_1$ and $ABS_2$ according to the time (tb−ta). The controller 13 judges success or failure of measurement based on the corrected absorbance $ABS_2$ of the control line CL, and references a calibration curve diagram prepared in advance to determine a total amount (concentration) of the antigen (or antibody) contained in the sample in accordance with the corrected absorbance $ABS_1$ of the test line TL and outputs this by a display device, printer, or other output device (step S12).

The coloration degrees of the test line TL and the control line CL formed in the detection portion 41b of the immunochromatographic test strip 41 are thus measured by the measuring method according to the present embodiment.

Effects obtained by the measuring method according to the present embodiment shall now be described. The present inventor noted that there is some form of correlation between fluctuation of coloration degree (reaction degree) at a colored line (reaction line) and fluctuation of flow speed (development speed) of the sample. As shown in FIG. 15, 13 immunochromatographic test strips M1 to M13 were actually prepared, and upon changing environmental conditions, etc., to change the flow speed among the immunochromatographic test strips M1 to M13, samples containing an antigen (or antibody) of the same concentration were dropped, and for each sample, the time ta, at which the sample passes through the first position on the immunochromatographic test strip, the time tb at which the sample passes through the second position, the difference (tb−ta), and the absorbance $ABS_1$ at the test line TL 15 minutes later were examined. In the example described below, nitrocellulose membranes treated with a surfactant were used as the immunochromatographic test strips, and samples, in each of which a protein was mixed at a concentration of 100 [ng/mol] in a phosphate buffer, were used.

Figure 16:
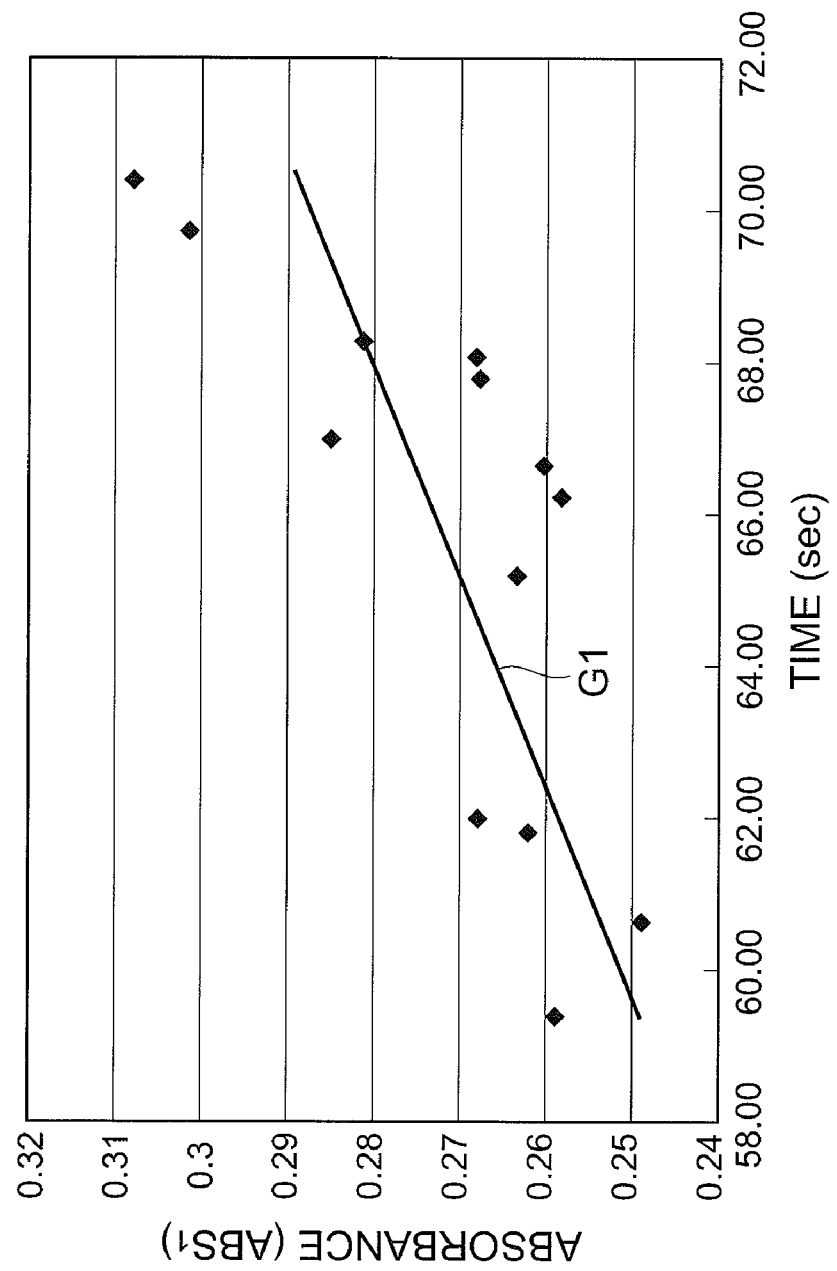
FIG. 16 is a diagram plotting absorbance and time (tb−ta) of the example along coordinate axes.

FIG. 16 is a diagram plotting the absorbance $ABS_1$ and the time (tb−ta) along coordinate axes. From FIG. 16, it can be understood that between the absorbance $ABS_1$ and the time (tb−ta), there is a correlation such that the longer the time (tb−ta), the greater the absorbance $ABS_1$. Thus, by expressing such a correlation by a first-order approximation line G1 as shown in FIG. 16 and correcting the absorbance $ABS_1$ based on the line G1, a more accurate absorbance $ABS_1$ that is suppressed in the influence of fluctuation of coloration degree is obtained.

In the present example, the first-order approximation line G1 is expressed by the following numerical formula (1):

$$ABS_1 = 0.0036 \times (tb-ta) + 0.0338 \quad (1)$$

Absorbances $ABS_1$ that were corrected using the following numerical formula (2) are shown in a rightmost column in FIG. 15:

$$(\text{Corrected } ABS_1) = (\text{Measured } ABS_1) - 0.0036 \times (tb-ta) \quad (2)$$

To evaluate the corrected absorbance $ABS_1$, coefficients of variation (fluctuation degrees) CV were computed respectively for the absorbance $ABS_1$ before correction and the absorbance $ABS_1$ after correction. As a result, the coefficient of variation CV of the absorbance $ABS_1$ before correction was 6.5, and the coefficient of variation CV of the absorbance $ABS_1$ after correction was 4.4, thus indicating that the fluctuation of the absorbance $ABS_1$ among the respective test strips M1 to M13 is reduced by the correction. Thus, by measuring the time (tb−ta), that is, the flow speed of the sample and correcting the absorbance (coloration degree) based on the measurement result, the influence due to the fluctuation of coloration degree can be suppressed and the amount of the antigen (or antibody) in the sample can be analyzed with good precision.

With the measuring method according to the present embodiment, by sensing the change of absorbance by detecting the reflected light while illuminating the measurement light on the first position (band-like region 41c) and thereafter sensing the change of absorbance by detecting the reflected light while illuminating the measurement light on the second position (band-like region 41d), timings at which the sample reaches the respective positions can be known readily. By then correcting the absorbances (coloration degrees) of the colored lines TL and CL based on the elapsed time (tb−ta) from the change of absorbance at the first position (band-like region 41c) to the change of absorbance at the second position (band-like region 41d), the influence due to the fluctuation of coloration degree can be suppressed and the amount of the antigen (or antibody) in the sample can be analyzed with good precision.

Also, as in the present embodiment, preferably the immunochromatographic test strip 41 has the band-like regions that cause antigen-antibody reactions with the sample (the two band-like regions 41c and 41d in the present embodiment) and the absorbances at the band-like regions 41c and 41d are acquired after elapse of the predetermined time longer than the time (tb–ta) from the change of absorbance at the first position (band-like region 41c). By thus acquiring the absorbances at the band-like regions 41c and 41d after the elapse of the predetermined time longer than (tb–ta) from the change of absorbance at the first position (band-like region 41c), because the antigen-antibody reactions proceed during this predetermined time and the colored lines TL and CL are expressed clearly, measurement of the coloration degree can be performed more precisely. Also, because the change of absorbance at the first position (band-like region 41c) is set as the start of measurement of the predetermined time, unlike a case of using a measurement starting input, such as pressing of a measurement starting button by an operator, etc., problems, such as fluctuation between an input timing and a timing at which measurement should actually be started, forgetting of input, etc., do not occur.

Also, as in the present embodiment, it is preferable to detect the reflected light continuously or intermittently by the photodetecting element 32 while scanning the measurement light of the light emitting element 31 in the sample flow direction so that the illumination position of the measurement light passes through the band-like regions 41c and 41d after the elapse of the predetermined time. Because the reflected light data of the band-like regions 41c and 41d that become the colored lines TL and CL and the peripheries thereof can thereby be acquired to enable preparation of an absorbance profile such as shown in FIG. 14, the absorbance (coloration degree) can be measured reliably even if errors occur in the positions of the colored lines TL and CL.

Also, as in the present embodiment, it is preferable to turn off the light emitting element 31 once after sensing of the change of absorbance at the second position (band-like region 41d) and to relight the light emitting element 31 thereafter to perform the operation of step S11 shown in FIG. 8 (the scanning of the measurement light of the light emitting element 31 in the sample flow direction to obtain the absorbance profile of the measurement light in the detection portion 41b). Because a lighting time of the light emitting element 31 can thus be shortened, power consumption can be suppressed and life of the light emitting element 31 can be extended. In a case where the predetermined time from the change of absorbance at the first position (band-like region 41c) to the performing of step S11 is approximately 15 minutes, the light emitting element 31 is relit, for example, at the point of elapse of approximately 14 minutes.

Also, as in the present embodiment, it is preferable to turn off the light emitting element 21 of the optical head 2 after sensing of the change of absorbance at the first position (band-like region 41c) by the optical head 2 and to thereafter light the light emitting element 31 of the optical head 3 to sense the change of absorbance at the second position (band-like region 41d). Because the light from the light emitting element 31 is thus not made incident on the photodetecting element 22 during sensing of the change of absorbance at the first position (band-like region 41c) and the light from the light emitting element 21 is not made incident on the photodetecting element 32 during sensing of the change of absorbance at the second position (band-like region 41d), detection precision of reflected light at each of the first and second positions can be improved.

Also, as in the present embodiment, it is preferable to use the light emitting elements 21 and 31 corresponding to the respective photodetecting elements 22 and 32 and for the photodetecting element 22 to detect the reflected light due to illumination by the light emitting element 21 and for the photodetecting element 32 to detect the reflected light due to illumination by the light emitting element 31. Light can thereby be illuminated with stability to each of the first position (band-like region 41c) and the second position (band-like region 41d), and detection precision of the change of absorbance and measurement precision of the flow speed of the sample can thereby be improved.

Also, as in the present embodiment, by the light emitting element 21 and the photodetecting element 22 being incorporated integrally in the optical head 2 and the light emitting element 31 and the photodetecting element 32 being incorporated integrally in the optical head 3, the light emitting element 21 and the photodetecting element 22 as well as the light emitting element 31 and the photodetecting element 32 are positioned with good precision with respect to each other and the detection precision of reflected light can be made high. Also, by at least one of the optical heads 2 and 3 (the optical head 3 in the present embodiment) having the member 35 (see FIG. 6) that surrounds the optical paths of the measurement light and the reflected light, incidence of noise light on the photodetecting element of the corresponding optical head can be prevented to further improve the detection precision of reflected light.

Also, preferably an interval between the optical head 2 and the optical head 3 in the present embodiment is variable. The interval between the optical head 2 and the optical head 3 can thereby be made to correspond readily to a size of the immunochromatographic test strip 41, etc.

Although in the present embodiment, the drive mechanism 12 moves both of the light emitting elements 21 and 31 and the setting plate 11 in a relative manner in the sample flow direction, just one of either of the light emitting elements 21 and 31 and the setting plate 11 may be moved in a relative manner in the sample flow direction instead. In this case, it is preferable to move the light emitting element for performing step S11 shown in FIG. 8 (the light emitting element 31 in the present embodiment) and the setting plate 11 in a relative manner.

Second Embodiment

Figure 17:
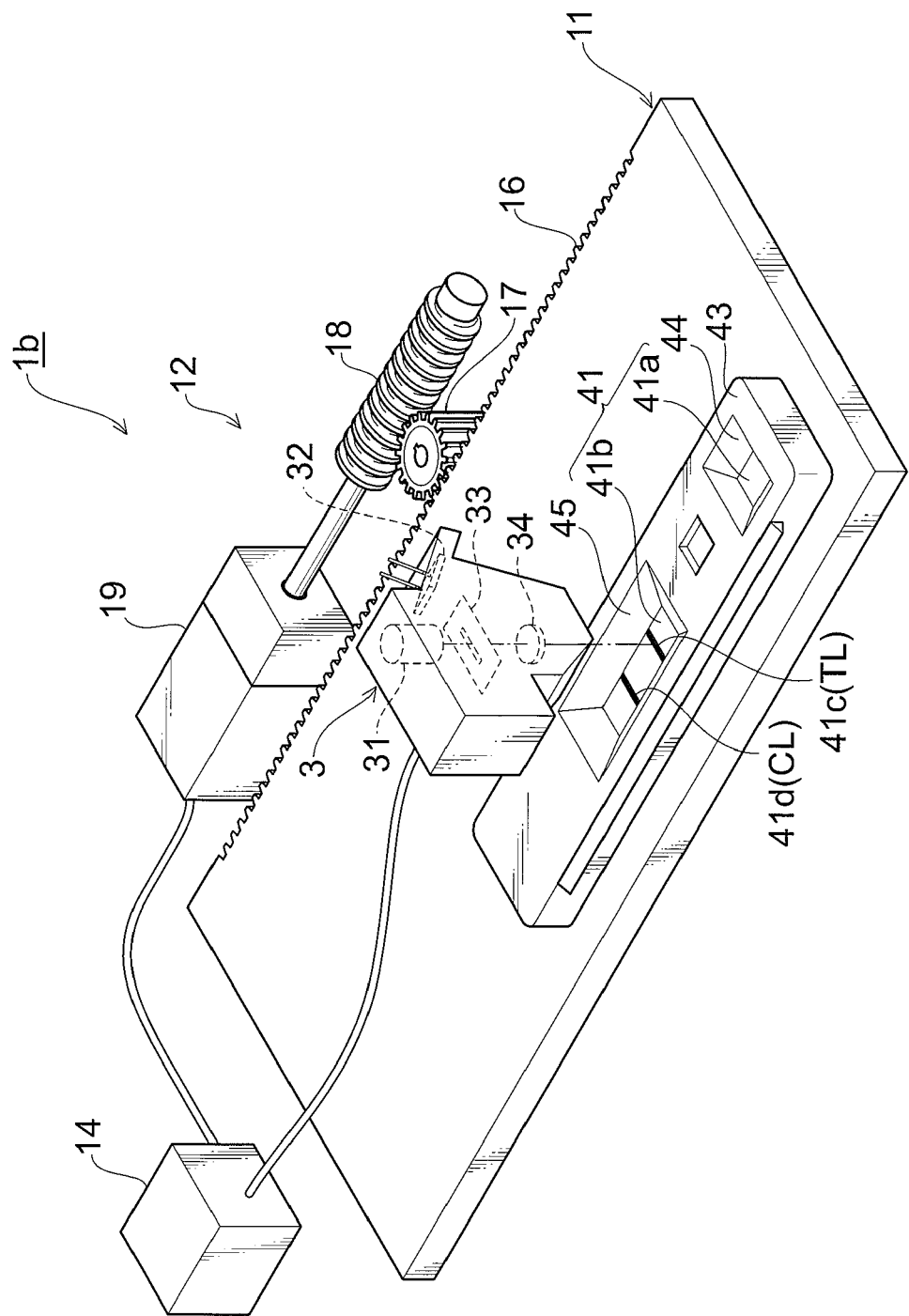
FIG. 17 is a perspective view of a configuration of a measuring apparatus used favorably in a method for measuring immunochromatographic test strip according to a second embodiment.

A method for measuring immunochromatographic test strip according to a second embodiment shall now be described. FIG. 17 is a perspective view of a configuration of a measuring apparatus 1b used favorably in the measuring method according to the present embodiment. A difference between the measuring apparatus 1b of the present embodiment and the first embodiment described above is the presence/non-presence of the first optical head. That is, the measuring apparatus 1b of the present embodiment does not have the optical head 2 such as shown in FIG. 1, and a controller 14 of the present embodiment performs sensing of a change of absorbance at the first position (band-like region 41c), sensing of a change of absorbance at the second position (band-like region 41d), and preparation of the absorbance profile of the measurement light using the optical head 3. The configurations of the optical head 3, the drive mechanism 12, and the immunochromatographic test utensil 42 in the present embodiment are the same as those of the first embodiment.

Figure 18:
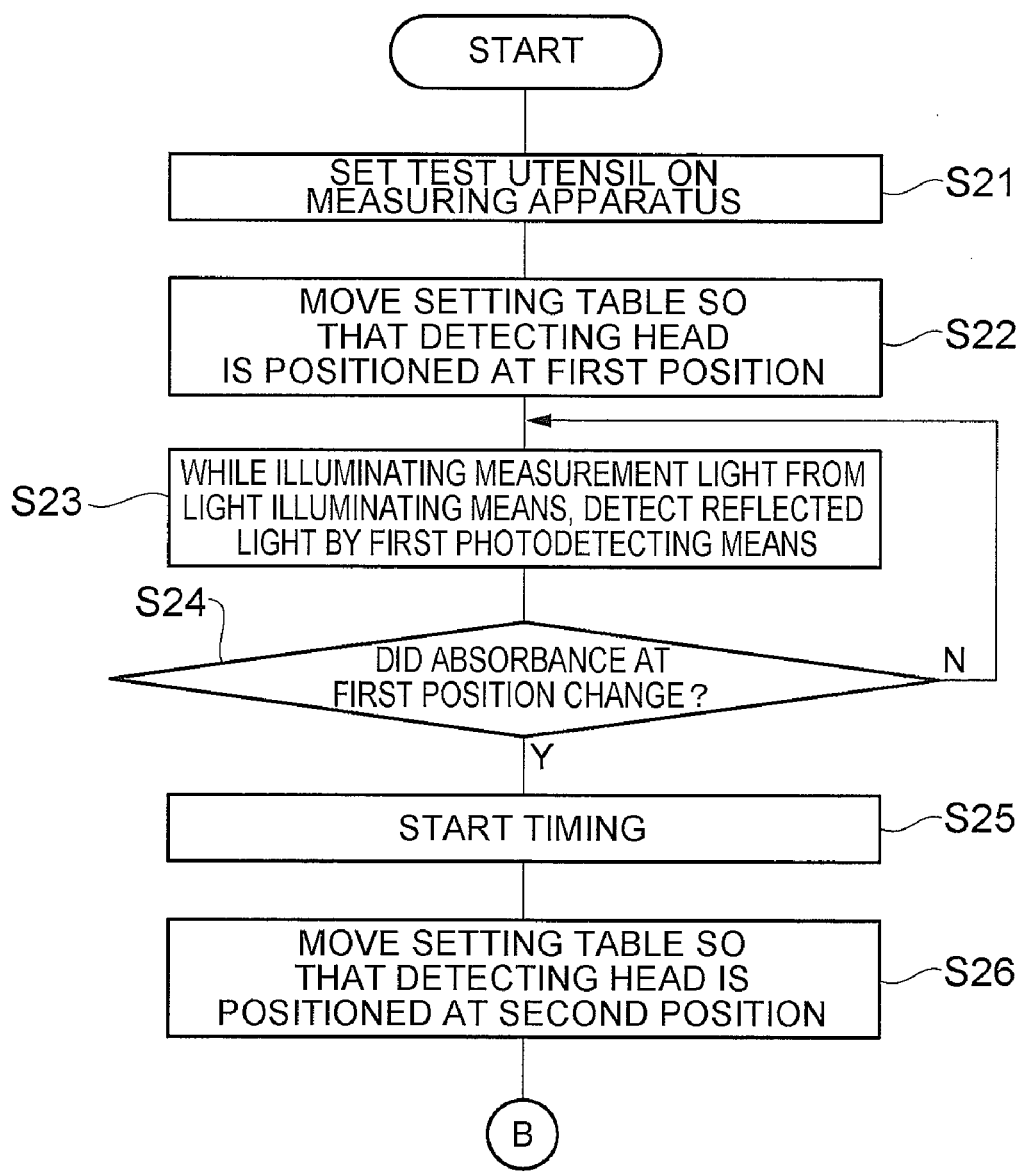
FIG. 18 is a flowchart of the measuring method according to the second embodiment.
Figure 19:
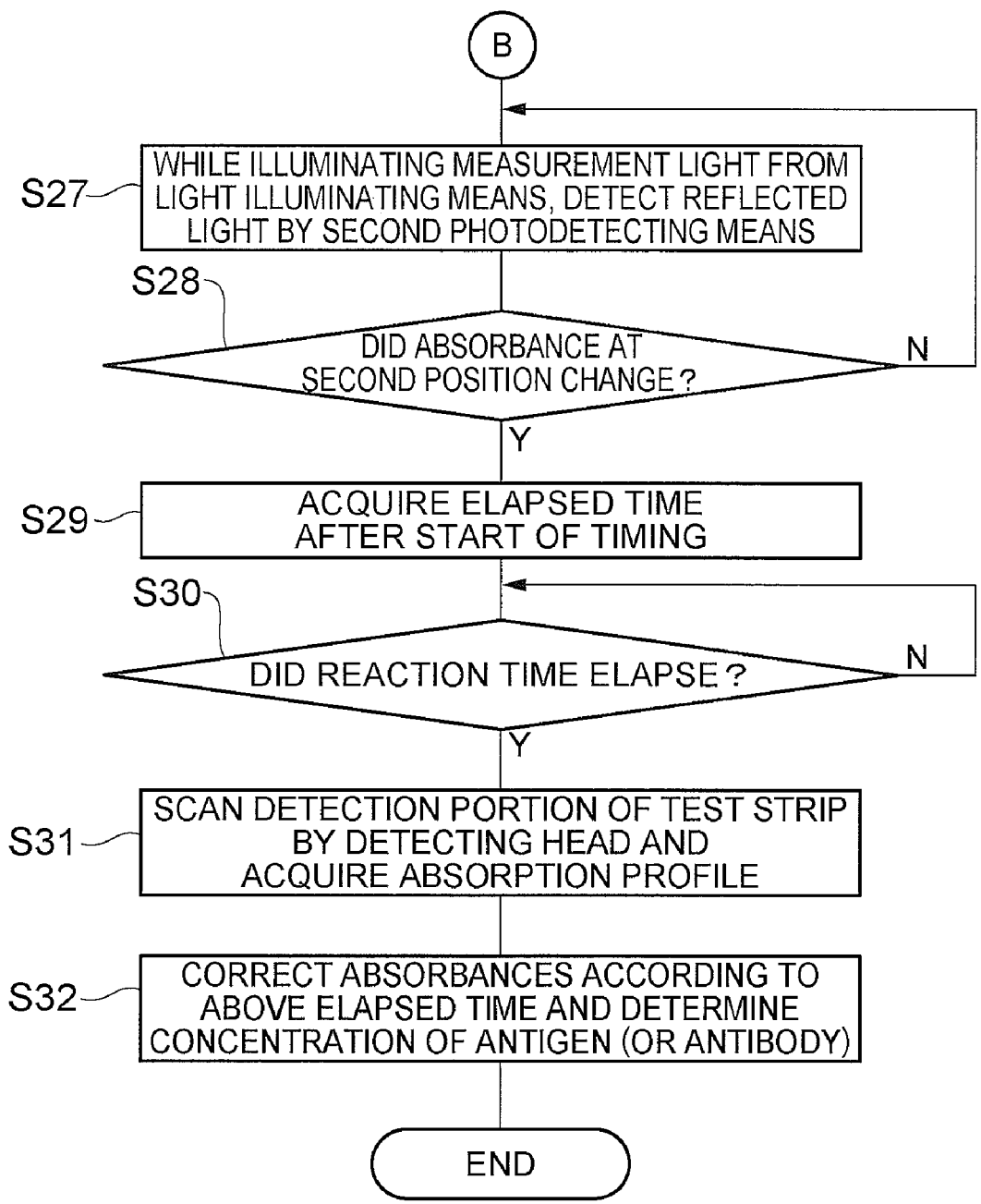
FIG. 19 is a flowchart of the measuring method according to the second embodiment.
Figure 20:
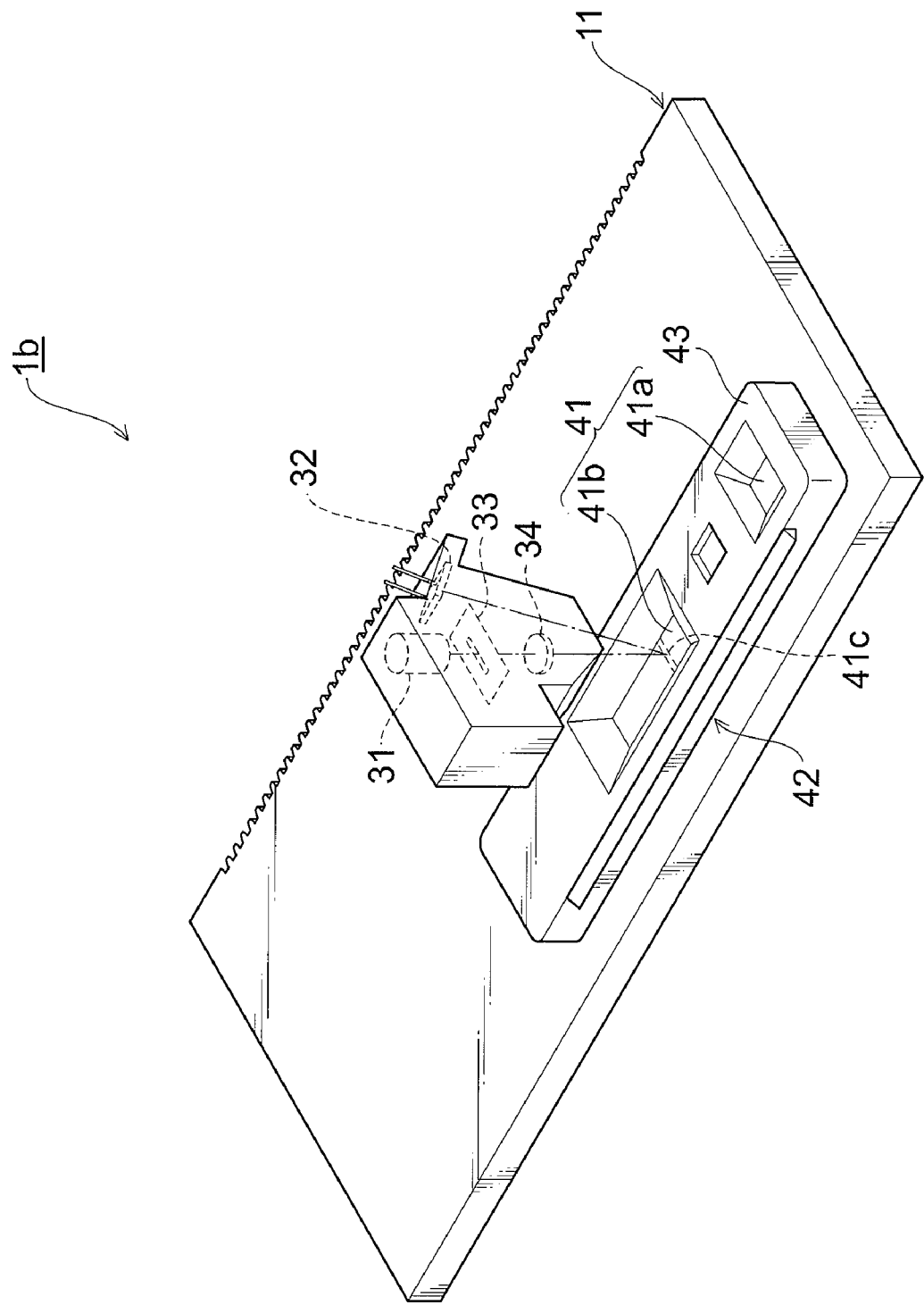
FIG. 20 is a perspective view for describing an operating state of the measuring apparatus of the second embodiment.
Figure 21:
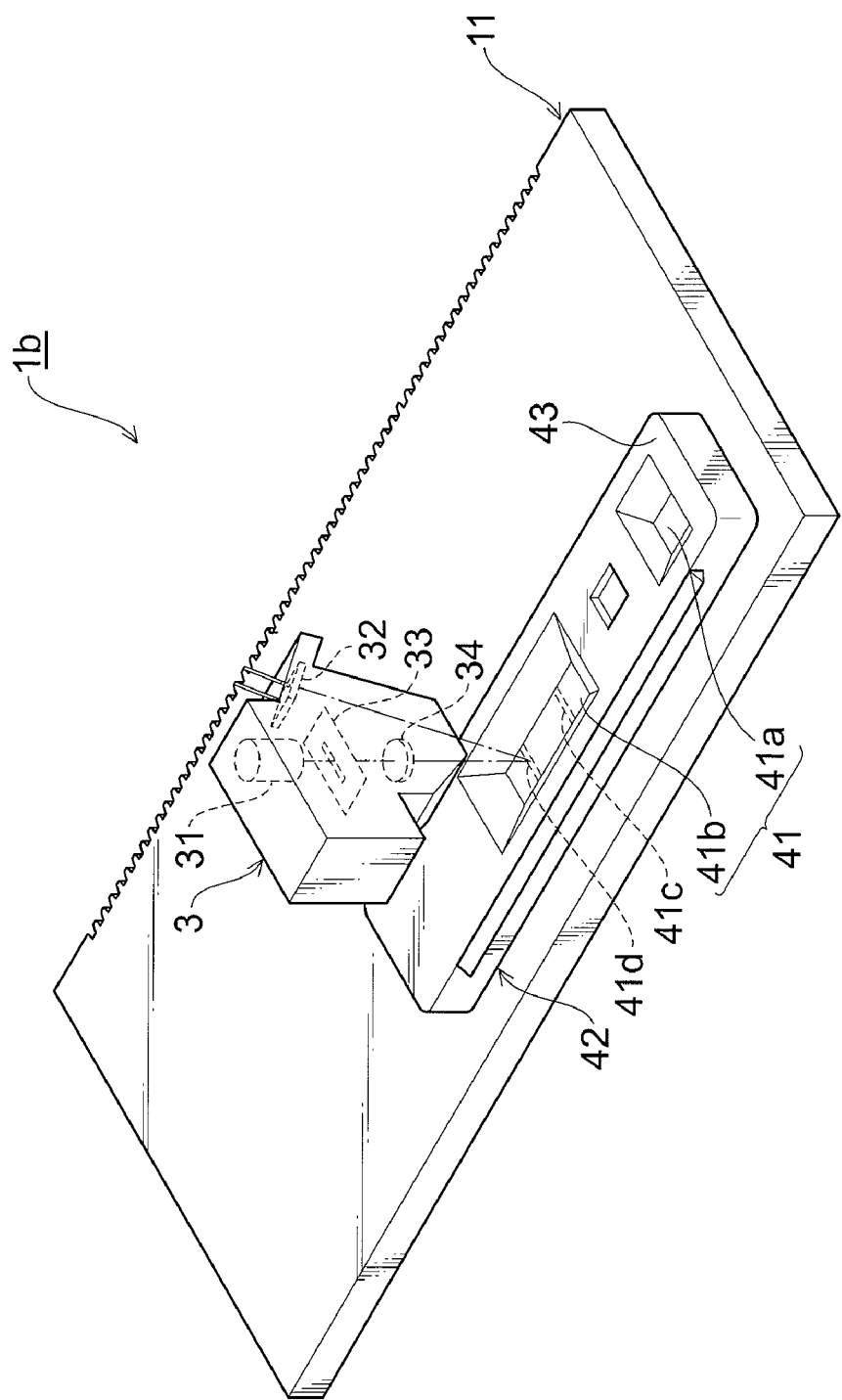
FIG. 21 is a perspective view for describing an operating state of the measuring apparatus of the second embodiment.

The method for measuring immunochromatographic test strip according to the present embodiment shall now be described with reference to FIGS. 18 to 23. FIGS. 18 and 19 are flowcharts of the measuring method according to the present embodiment. FIGS. 20 to 23 are perspective views for describing operating states of the measuring apparatus 1b. In FIGS. 20 to 23, the drive mechanism 12 and the controller 14 shown in FIG. 17 are omitted from illustration.

First, a measurer sets the immunochromatographic test utensil 42 on the setting plate 11 (step S21). The controller 14 then moves the setting plate 11 and the optical head 3 in a relative manner so as to detect the reflected light from the first position (band-like region 41c) on the immunochromatographic test strip 41. Specifically, the controller 14 moves the setting plate 11 by actuating the drive mechanism 12 and thereby controls the relative positional relationship of the optical head 3 and the immunochromatographic test strip 41 so that the first position (band-like region 41c) on the immunochromatographic test strip 41 is positioned in the light emitting direction of the light emitting element 31 of the optical head 3 (see FIG. 20) (step S22).

Next, after the measurer drops a sample onto the sample application portion 41a, the light emitting element 31 illuminates the measurement light on the first position (band-like region 41c) of the immunochromatographic test strip 41. The photodetecting element 32 receives the reflected light and converts it to an electrical signal that is in accordance with the light intensity. The electrical signal is transmitted to the controller 14, and based on this electrical signal, the controller 14 senses the reflected light intensity at the first position (band-like region 41c) (step S23). The controller 14 observes the change of optical characteristic (absorbance) based on the electrical signal (step S24) and starts timing at the time to at which the absorbance changed (step S25).

Subsequently, the controller 14 moves the setting plate 11 and the optical head 3 in a relative manner so as to detect the reflected light from the second position (band-like region 41d) on the immunochromatographic test strip 41. That is, the controller 14 moves the setting plate 11 by actuating the drive mechanism 12 again and thereby controls the relative positional relationship of the optical head 3 and the immunochromatographic test strip 41 so that the second position (band-like region 41d) on the immunochromatographic test strip 41 is positioned in the light emitting direction of the light emitting element 31 of the optical head 3 (see FIG. 21) (step S26). Thereafter, the light emitting element 31 illuminates the measurement light on the second position (band-like region 41d), and the photodetecting element 32 outputs the electrical signal that is in accordance with the reflected light intensity. Based on this electrical signal, the controller 14 senses the reflected light intensity at the second position (band-like region 41d) (step S27). The controller 14 observes the change of optical characteristic (absorbance) based on the electrical signal (step S28) and acquires the difference (tb–ta) between the time tb at which the absorbance changed and the time ta (step S29). After the absorbance has changed at the second position (band-like region 41d), the controller 14 turns off the light emitting element 31 once.

Figure 22:
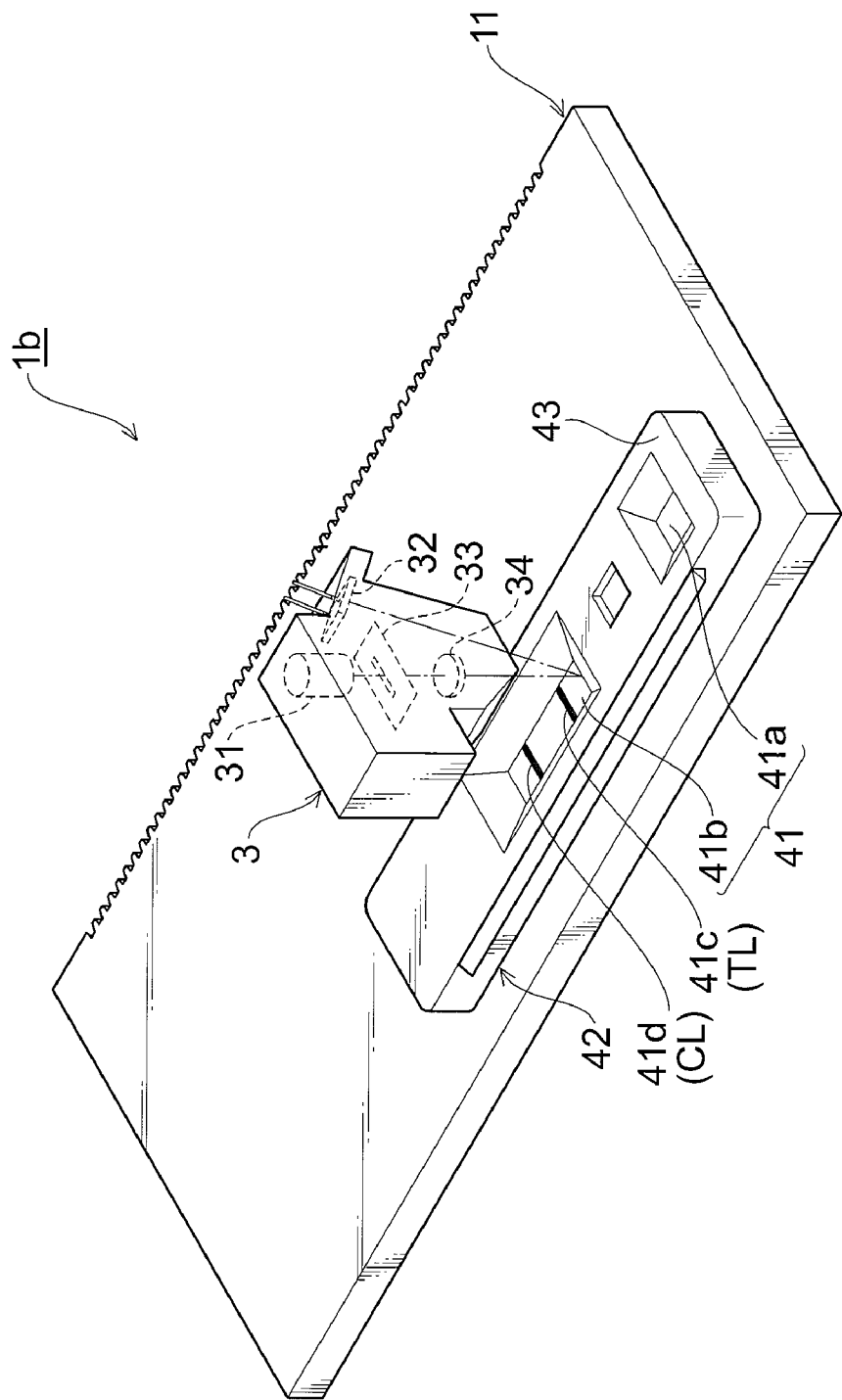
FIG. 22 is a perspective view for describing an operating state of the measuring apparatus of the second embodiment.
Figure 23:
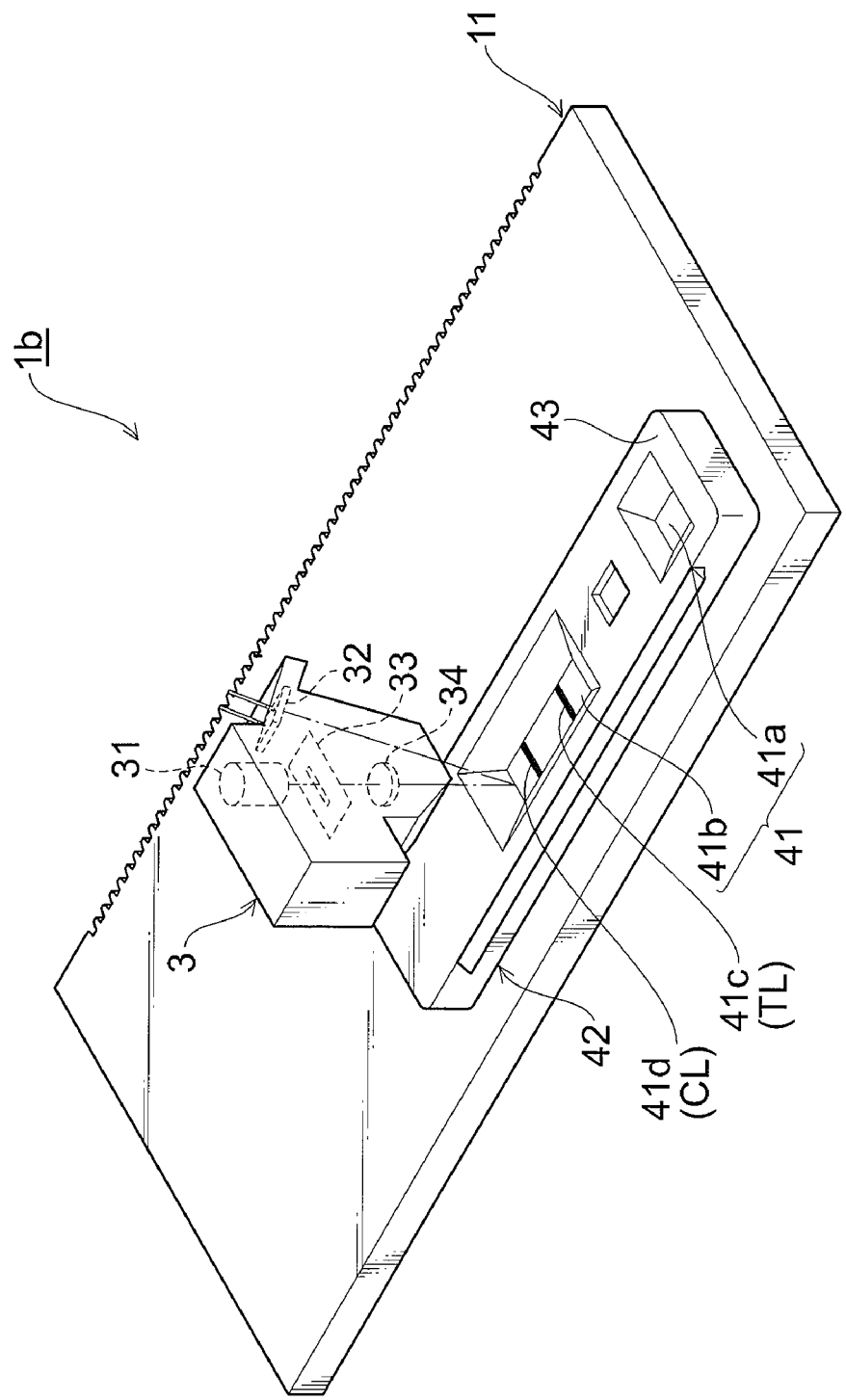
FIG. 23 is a perspective view for describing an operating state of the measuring apparatus of the second embodiment.

The controller 14 then performs counting of the predetermined time from the time ta (step S30). During this predetermined time, the band-like regions 41c and 41d become colored and the colored lines TL and CL become expressed. After the elapse of the predetermined time, the controller 14 relights the light emitting element 31, and while scanning the measurement light of the light emitting element 31 in the sample flow direction so that the illumination position of the measurement light passes through the band-like regions 41c and 41d, detects the reflected light by the photodetecting element 32 continuously (or intermittently), and obtains the absorbance profile of the measurement light of the detection portion 41b (step S31). That is, the controller 14 actuates the drive mechanism 12 again to move the setting plate 11 and makes the end at the upstream side of the detection portion 41b be positioned in the light emitting direction of the light emitting element 31 as shown in FIG. 22. Then while moving the illumination position of the measurement light toward the downstream side (that is, while moving the immunochromatographic test strip 41 to the upstream side relative to the optical head 3) until the end at the downstream side of the detection portion 41b is positioned in the light emitting direction of the light emitting element 31 (see FIG. 23), the controller 14 makes the light emitting element 31 illuminate the measurement light and acquires the electrical signal that is in accordance with the reflected light intensity by the photodetecting element 32.

The controller 14 then prepares the absorbance profile (see FIG. 13), and from the absorbance profile, computes the absorbance $ABS_1$ of the test line TL and the absorbance $ABS_2$ of the control line CL on the immunochromatographic test strip 41. Then, based on a relationship formula set in advance, the controller 14 corrects the absorbances $ABS_1$ and $ABS_2$ according to the time (tb–ta). The controller 14 judges success or failure of measurement based on the corrected absorbance $ABS_2$ of the control line CL, and references a calibration curve diagram prepared in advance to determine a total amount (concentration) of the antigen (or antibody) contained in the sample in accordance with the corrected absorbance $ABS_1$ of the test line TL and outputs this by the display device, printer, or other output device (step S32).

The coloration degrees of the test line TL and the control line CL formed in the detection portion 41b of the immunochromatographic test strip 41 are thus measured by the measuring method according to the present embodiment.

As in the measuring method according to the present embodiment, an illuminating unit (the light emitting element 31) in common may be used to illuminate the measurement light on the first position (band-like region 41c) and the second position (band-like region 41d). Even with such a configuration, by sensing the change of absorbance at the first position (band-like region 41c) and sensing the change of absorbance at the second position (band-like region 41d), the timings to and tb at which the sample reaches the respective positions can be known readily. By then correcting the absorbances (coloration degrees) of the colored lines TL and CL based on the elapsed time (tb–ta), the influence due to the fluctuation of coloration degree can be suppressed and the amount of the antigen (or antibody) in the sample can be analyzed with good precision.

Modification Examples

Figure 24:
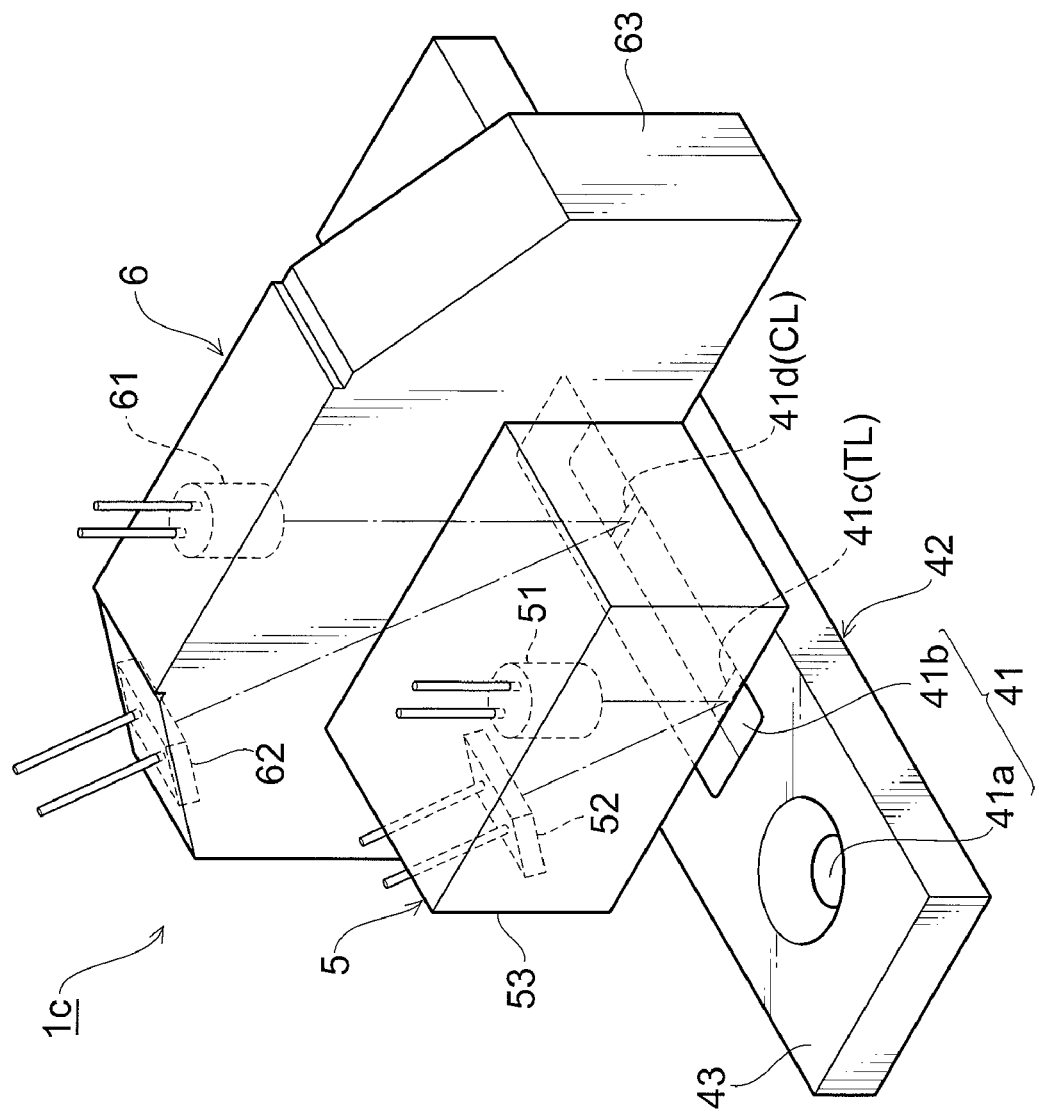
FIG. 24 is a perspective view of a measuring apparatus used favorably in the measuring method according to the first embodiment.

FIG. 24 is a perspective view of a configuration of a measuring apparatus 1c favorable for putting the measuring method according to the first embodiment into practice. The measuring apparatus 1c includes optical heads 5 and 6. A light emitting element 51 and a photodetecting element 52 are integrally incorporated in the optical head 5. A light emitting element 61 and a photodetecting element 62 are integrally incorporated in the optical head 6.

The optical head 5 furthermore includes an unillustrated beam shaping member and lens for shaping measurement light emitted from the semiconductor light emitting element 51 to slit light substantially parallel to the band-like region 41c, and the semiconductor light emitting element 51, the semiconductor photodetecting element 52, the beam shaping member, and the lens are integrally held and defined in mutual positional relationship by a block-like member 53. The light emitting element 51 is held by the member 53 so that a light emitting direction thereof is perpendicular to the top surface of the immunochromatographic test strip 41 and illuminates the measurement light on the first position (band-like region 41c) of the immunochromatographic test strip 41. The photodetecting element 52 is disposed obliquely upward in a direction substantially parallel to the band-like region 41c from the first position (band-like region 41c) and converts reflected light from the first position (band-like region 41c) of the immunochromatographic test strip 41 to an electrical signal that is in accordance with the intensity of the reflected light.

The optical head 6 furthermore includes an unillustrated beam shaping member and lens for shaping measurement light emitted from the semiconductor light emitting element 61 to slit light substantially parallel to the band-like region 41d, and the semiconductor light emitting element 61, the semiconductor photodetecting element 62, the beam shaping member, and the lens are integrally held and defined in mutual positional relationship by a block-like member 63. The light emitting element 61 is held by the member 63 so that a light emitting direction thereof is perpendicular to the top surface of the immunochromatographic test strip 41 and illuminates the measurement light on the second position (band-like region 41d) of the immunochromatographic test strip 41. That is, an interval between an emission optical axis of the light emitting element 61 and an emission optical axis of the light emitting element 51 is set substantially equal to the interval between the first position (band-like region 41c) and the second position (band-like region 41d). The photodetecting element 62 is disposed obliquely upward in a direction substantially parallel to the band-like region 41d from the second position (band-like region 41d) and converts reflected light from the second position (band-like region 41d) of the immunochromatographic test strip 41 to an electrical signal that is in accordance with the intensity of the reflected light.

Each of the members 53 and 63 has two unillustrated holes of the same configuration as the holes 35a and 35b shown in FIG. 6 that make up baffle structures. One of the holes surrounds the optical path of the measurement light emitted from the light emitting element 51 (or 61), and the other hole surrounds an optical path of light reflected from the immunochromatographic test strip 41 and made incident on the photodetecting element 52 (or 62).

In the present modification example, unlike the first embodiment, the first optical head 5 is also configured with the baffle structures with the member 53 surrounding the optical path of the measurement light from the light emitting element 51 and the optical path of the reflected light from the first position (band-like region 41c). By thus surrounding the optical paths of the measurement light and the reflected light in at least one of the two optical heads, incidence of noise light on the photodetecting unit of the corresponding optical head can be prevented to further improve the detection precision of reflected light.

Also, as in the present modification example, the interval between the emission optical axis of the light emitting element 51 and the emission optical axis of the light emitting element 61 may be set in accordance with the interval between the first position and the second position of the immunochromatographic test strip.

Figure 25:
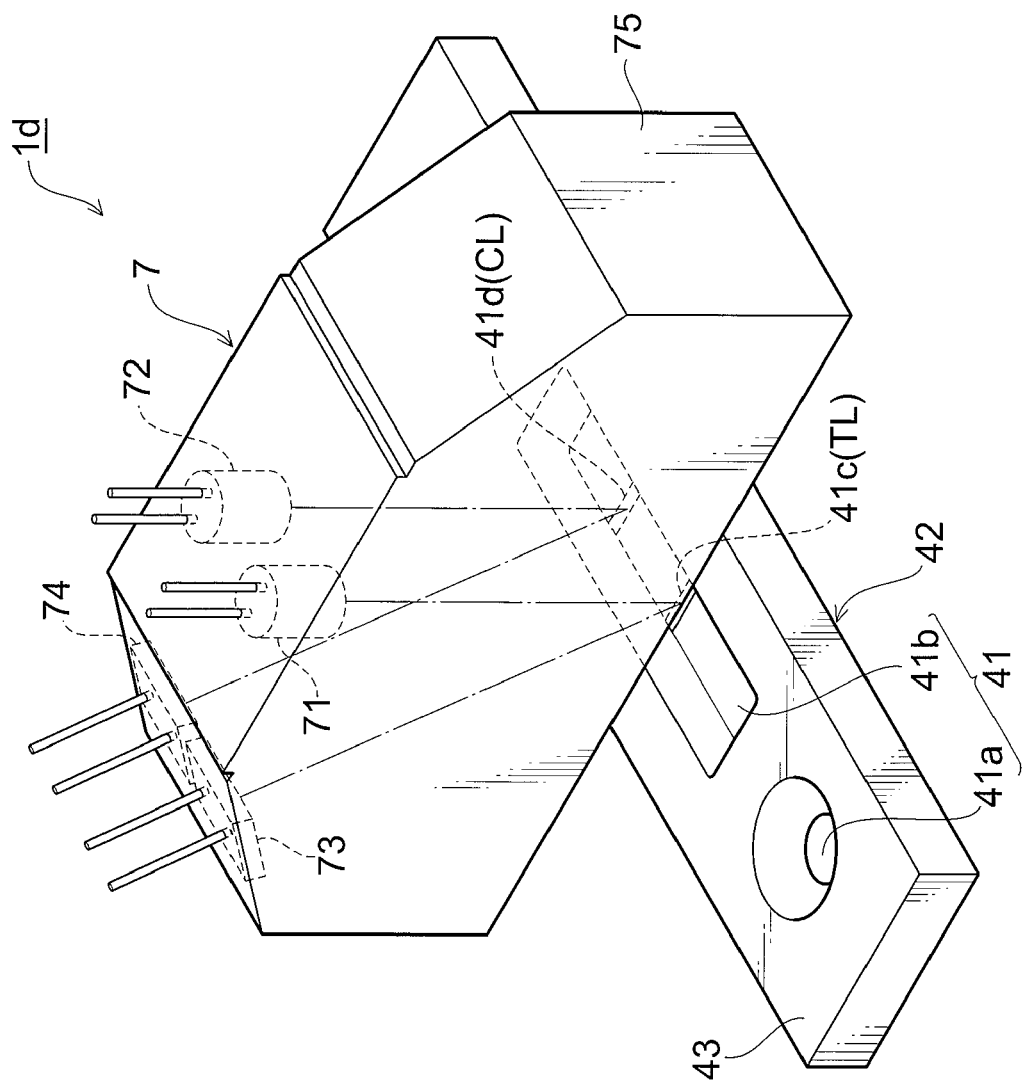
FIG. 25 is a perspective view of a measuring apparatus used favorably in the measuring method according to the first embodiment.

FIG. 25 is a perspective view of a measuring apparatus 1d favorable for putting the measuring method according to the first embodiment into practice. The measuring apparatus 1d includes an optical head 7 that is fixed in relative position with respect to the immunochromatographic test strip 41. Light emitting elements 71 and 72 and photodetecting elements 73 and 74 are integrally incorporated in the optical head 7 and thereby defined in mutual positional relationship.

The light emitting elements 71 and 72 are held by a member 75 so that light emitting directions thereof are perpendicular to the top surface of the immunochromatographic test strip 41. The light emitting element 71 illuminates measurement light on the first position (band-like region 41c) of the immunochromatographic test strip 41, and the light emitting element 72 illuminates measurement light on the second position (band-like region 41d). The photodetecting element 73 is disposed obliquely upward in a direction substantially parallel to the band-like region 41c from the first position (band-like region 41c) and converts reflected light from the first position (band-like region 41c) to an electrical signal that is in accordance with the intensity of the reflected light. The photodetecting element 74 is disposed obliquely upward in a direction substantially parallel to the band-like region 41d from the second position (band-like region 41d) of the immunochromatographic test strip 41 and converts reflected light from the second position (band-like region 41d) to an electrical signal that is in accordance with the intensity of the reflected light.

The member 75 has baffle structures of the same configuration as those of the member 35 shown in FIG. 6, and includes a hole surrounding the optical path of the measurement light emitted from the light emitting element 71, a hole surrounding the optical path of the measurement light emitted from the light emitting element 72, a hole surrounding an optical path of the light reflected from the first position (band-like region 41c) and made incident on the photodetecting element 73, and a hole surrounding an optical path of the light reflected from the second position (band-like region 41d) and made incident on the photodetecting element 74.

In the present modification example, because unlike the first embodiment, the light emitting elements 71 and 72 and the photodetecting elements 73 and 74 are integrally incorporated in a single optical head 7, the light emitting element 71 and the photodetecting element 73 as well as the light emitting element 72 and the photodetecting element 74 are positioned with good precision with respect to each other and the detection precision of reflected light can thus be improved. Also, because the optical head 7 has the member 75 that surrounds the optical paths of the measurement light and the reflected light, incidence of noise light on the photodetecting elements 73 and 74 can be prevented to improve the detection precision of reflected light.

Third Embodiment

Figure 26:
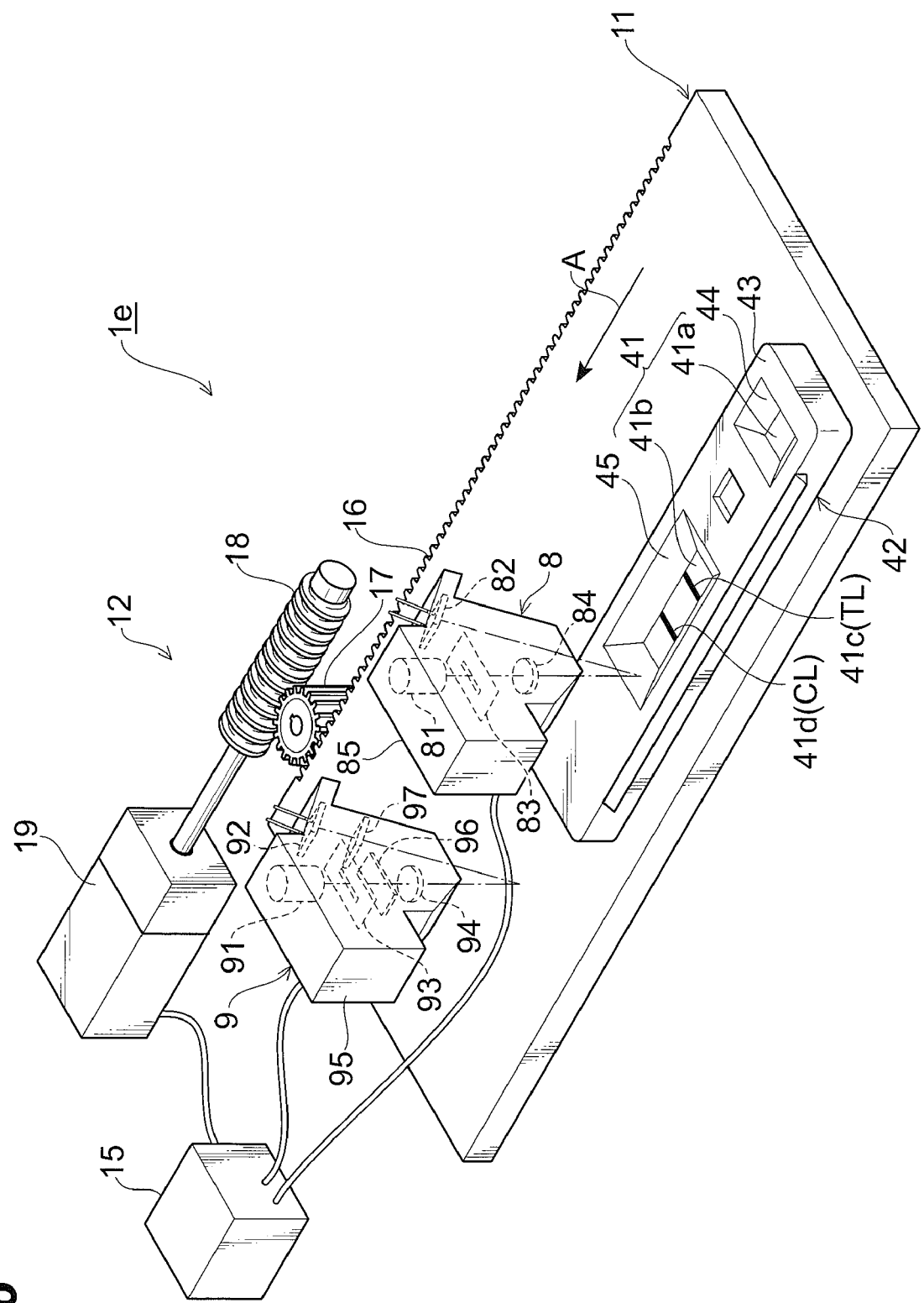
FIG. 26 is a perspective view of a configuration of a measuring apparatus used favorably in a method for measuring immunochromatographic test strip according to a third embodiment.

A method for measuring immunochromatographic test strip according to a third embodiment shall now be described. FIG. 26 is a perspective view of a configuration of a measuring apparatus 1e used favorably in the method for measuring immunochromatographic test strip according to the present embodiment. The measuring apparatus 1e of the present embodiment illuminates measurement light (excitation light) on reaction lines (test line TL and control line CL) formed by dropping of a sample on the immunochromatographic test strip 41 containing a fluorescent substance and measures the reaction degrees of the reaction lines TL and CL by detecting intensities of fluorescence generated at the reaction lines TL and CL. As with the dye in the first embodiment, the fluorescent substance in the present embodiment labels an antibody (or antigen), coated on the immunochromatographic test strip 41 and binding with an antigen (or antibody) in the sample, and the reactions at the test line TL and the control line CL are the same as those in the first embodiment.

A main difference between the measuring apparatus 1e of the present embodiment and the first embodiment is a configuration of an optical head. That is, an optical head 8, which is a first optical head in the present embodiment, has the same configuration as the optical head 3 of the first embodiment. An optical head 9, which is a second optical head in the present embodiment, has a configuration for illuminating excitation light as measurement light on the reaction lines TL and CL formed in the immunochromatographic test strip 41 and detecting the intensity of the fluorescence generated at the reaction lines TL and CL. Configurations of the drive mechanism 12 and the immunochromatographic test utensil 42 in the present embodiment are the same as those of the first embodiment.

As shown in FIG. 26, the measuring apparatus 1e includes: the setting plate (test strip support) 11, for supporting the immunochromatographic test utensil 42 that has the immunochromatographic test strip 41; the first optical head 8, integrally incorporating a light emitting element (first light illuminating unit) 81, which illuminates the measurement light on the immunochromatographic test strip 41, and a photodetecting element (first photodetecting unit) 82, which detects the reflected light from the immunochromatographic test strip 41; the second optical head 9, integrally incorporating a light emitting element (second light illuminating unit) 91, which illuminates the measurement light (excitation light) on the immunochromatographic test strip 41, and a photodetecting element (second photodetecting unit) 92, which detects the fluorescence from the immunochromatographic test strip 41; the drive mechanism 12, moving the setting plate 11 in the sample flow direction relative to the optical heads 8 and 9; and a controller 15, controlling the optical heads 8 and 9 and the drive mechanism 12. Because the configurations of the setting plate 11, the drive mechanism 12, and the immunochromatographic test strip 41 are the same as in the first embodiment, detailed description thereof shall be omitted.

The optical head 8 has the same configuration as the optical head 3 of the first embodiment. That is, the optical head 8 has the light emitting element 81, the photodetecting element 82, a beam shaping member 83, and a lens 84, and these are held integrally and defined in mutual positional relationship by a member 85. A semiconductor light emitting element, such as a light emitting diode (LED), is used as the light emitting element 81, and a semiconductor photodetecting element, such as a silicon (Si) photodiode, is used as the photodetecting element 82. The light emitting element 81 is held by the member 85 so that an optical axis thereof is perpendicular to the top surface of the immunochromatographic test strip 41 and illuminates the measurement light on the immunochromatographic test strip 41. The photodetecting element 82 is disposed obliquely upward in a direction substantially parallel to the band-like regions 41c and 41d (see FIG. 2) from the illumination position of the measurement light on the immunochromatographic test strip 41 and converts the reflected light from the immunochromatographic test strip 41 to an electrical signal that is in accordance with the intensity of the reflected light.

The optical head 9 has substantially the same configuration as the optical head 8. That is, the optical head 9 has the light emitting element 91, the photodetecting element 92, a beam shaping member 93, and a lens 94, and these are held integrally and defined in mutual positional relationship by a member 95. However, a wavelength filter 96 is disposed between the beam shaping member 93 and the lens 94. The wavelength filter 96 takes out, from the light emitted from the light emitting element 91, a wavelength component necessary for excitation of the fluorescent substance. Also, a wavelength filter 97 is disposed between the photodetecting element 92 and the immunochromatographic test strip 41. The wavelength filter 97 makes just the fluorescence be incident on the photodetecting element 92 and cuts light of other wavelength ranges (light emitted from the light emitting element 91, etc.). The light emitting element 91 illuminates the immunochromatographic test strip 41 with the measurement light (excitation light) for exciting the fluorescent substance. The photodetecting element 92 converts the fluorescence from the immunochromatographic test strip 41 to an electrical signal that is in accordance with an intensity of the fluorescence.

Figure 27:
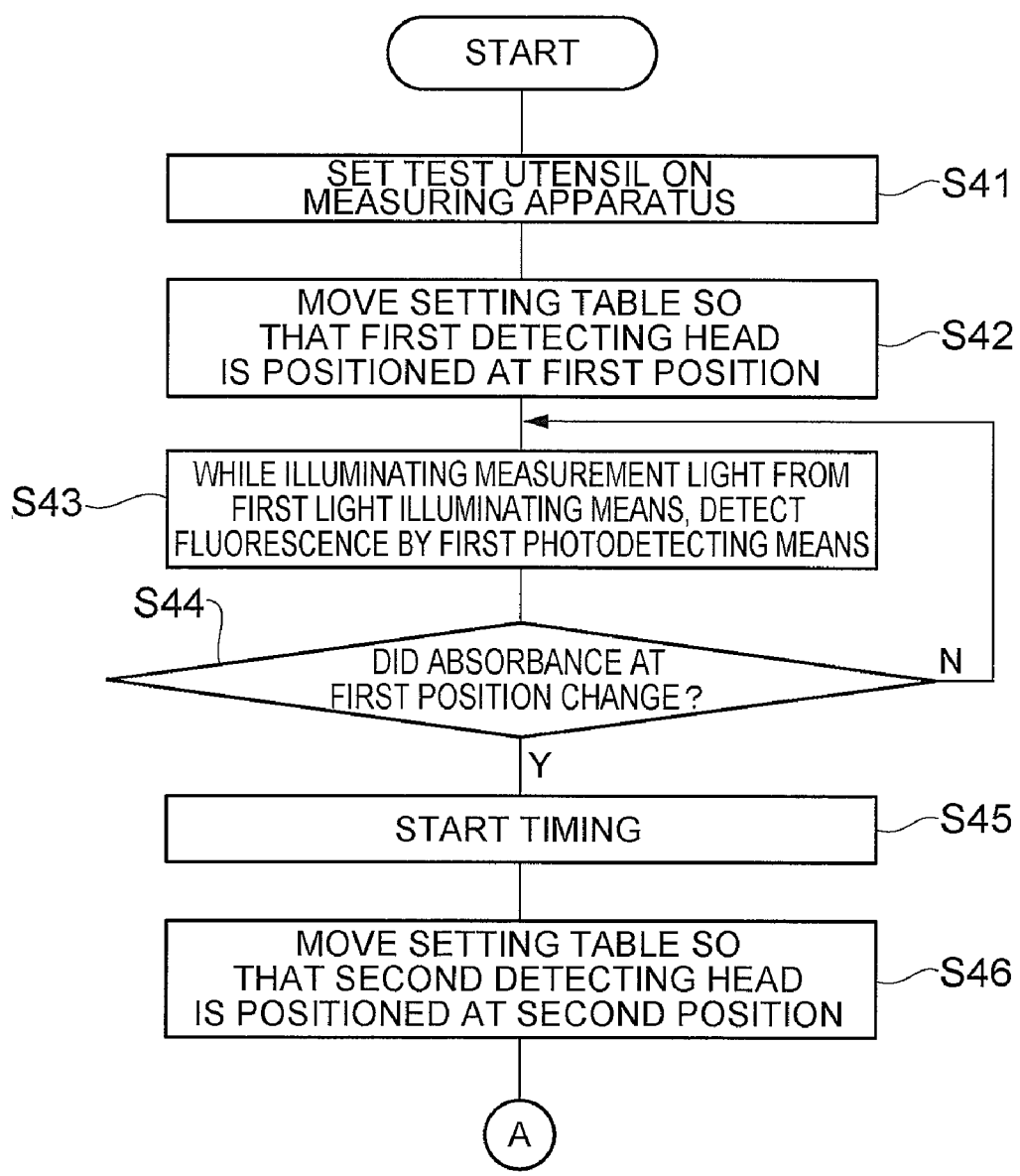
FIG. 27 is a flowchart of the measuring method according to the third embodiment.
Figure 28:
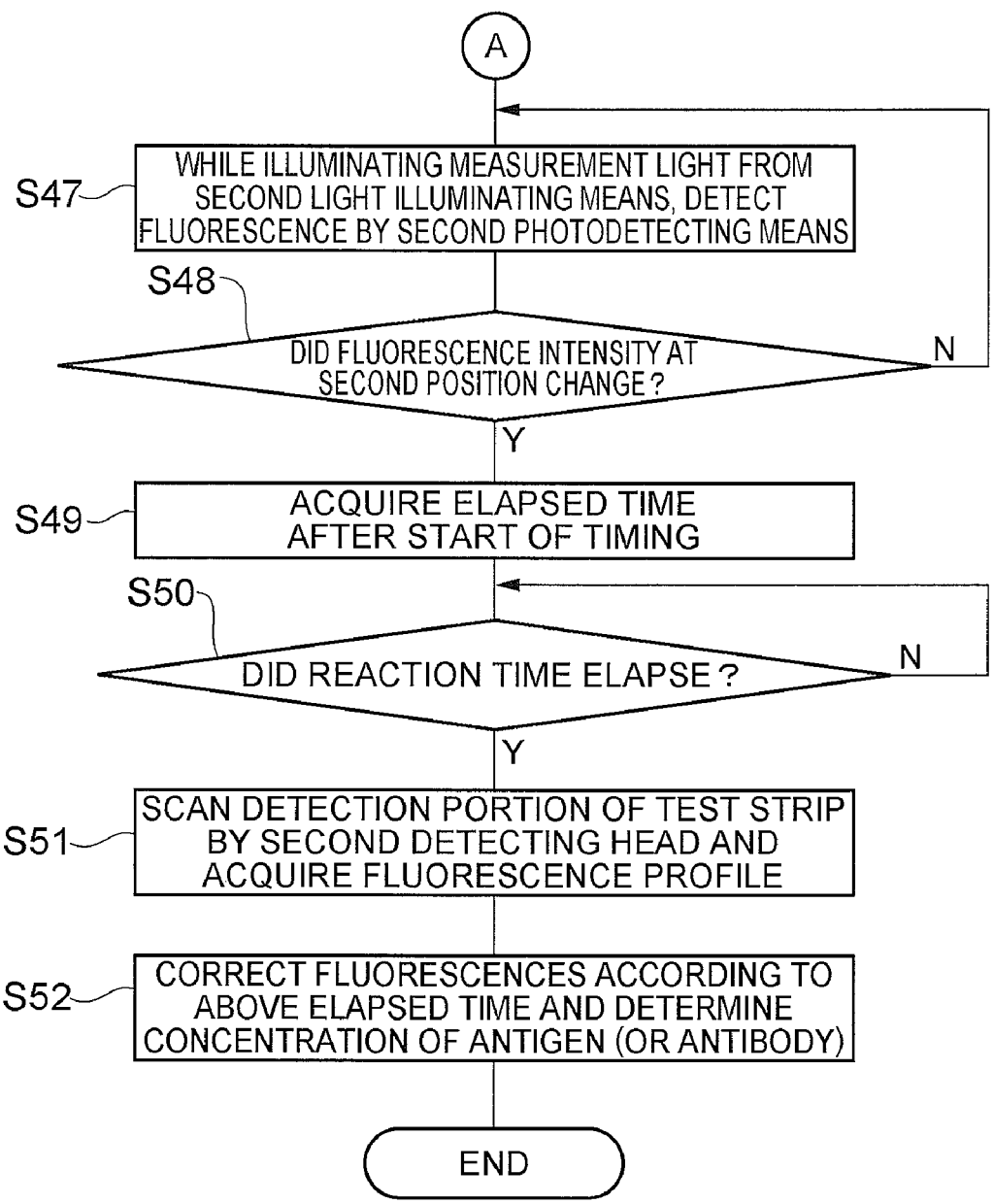
FIG. 28 is a flowchart of the measuring method according to the third embodiment.

The method for measuring immunochromatographic test strip according to the present embodiment shall now be described with reference to FIGS. 27 to 32. FIGS. 27 and 28 are flowcharts of the measuring method according to the present embodiment. FIGS. 29 to 32 are perspective views for describing operating states of the measuring apparatus 1e. In FIGS. 29 to 32, the drive mechanism 12 and the controller 15 shown in FIG. 26 are omitted from illustration.

Figure 29:
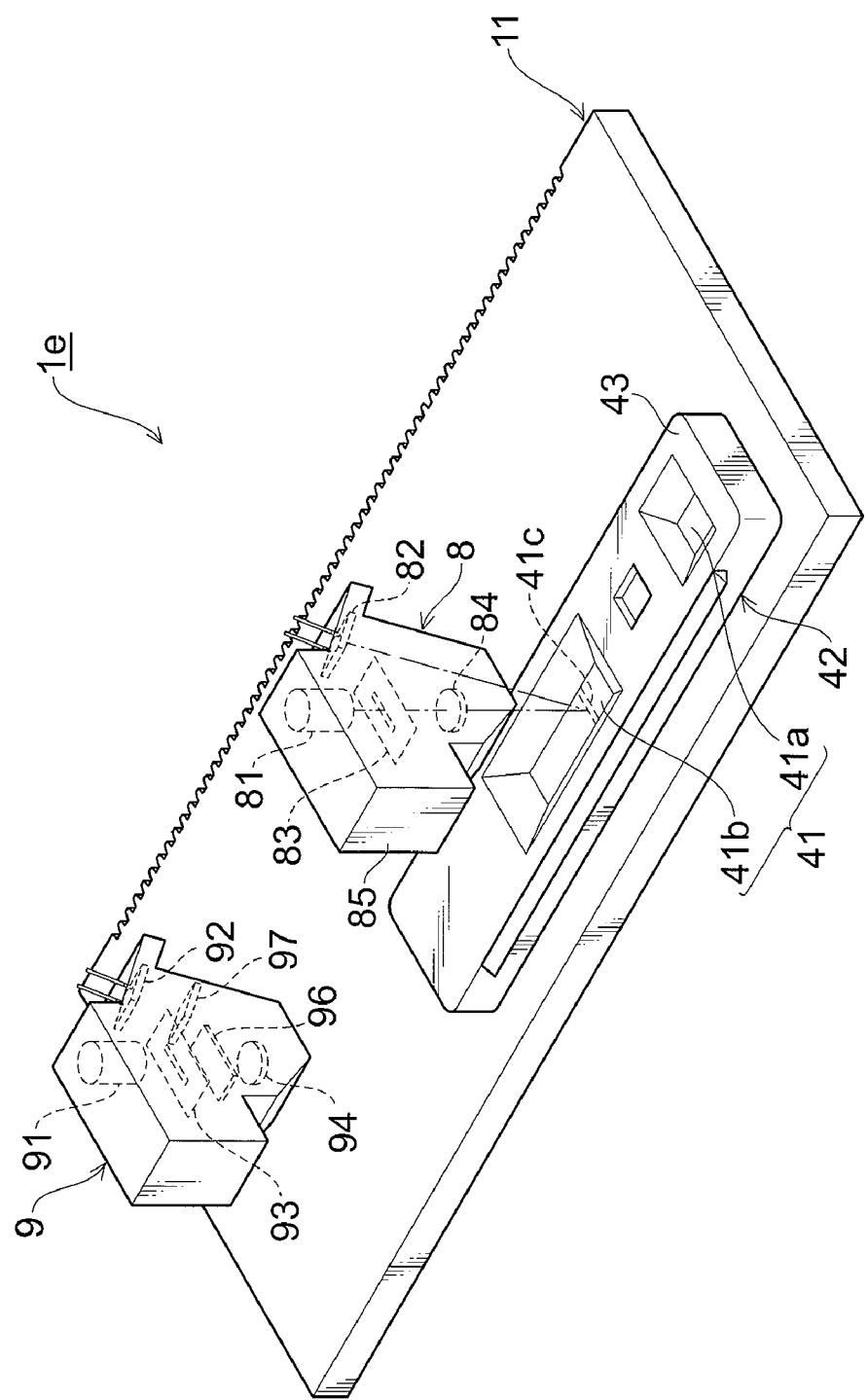
FIG. 29 is a perspective view for describing an operating state of the measuring apparatus of the third embodiment.

First, a measurer sets the immunochromatographic test utensil 42 on the setting plate 11 (step S41). The controller 15 then moves the setting plate 11 and the optical head 8 in a relative manner so as to detect the reflected light from a first position of the immunochromatographic test strip 41 determined in advance. Specifically, the controller 15 moves the setting plate 11 by actuating the drive mechanism 12 and thereby controls the relative positional relationship of the optical head 8 and the immunochromatographic test strip 41 so that the first position on the immunochromatographic test strip 41 is positioned in a light emitting direction of the light emitting element 81 of the optical head 8 (step S42). In the present embodiment, the first position on the immunochromatographic test strip 41 is set inside the first band-like region 41c. Thus, as shown in FIG. 29, the band-like region 41c is positioned in the light emitting direction of the light emitting element 81.

Next, after the measurer drops a sample onto the sample application portion 41a, the light emitting element 81 illuminates the measurement light on the first position (that is, the band-like region 41c) of the immunochromatographic test strip 41. The photodetecting element 82 receives the reflected light and converts it to an electrical signal that is in accordance with the light intensity. The electrical signal is transmitted to the controller 15, and based on this electrical signal, the controller 15 senses the reflected light intensity at the first position (band-like region 41c) (step S43). The light emitting element 91 is unlit at this point.

FIG. 33(a) is a schematic graph showing a manner of change of an optical characteristic (absorbance) at the first position (band-like region 41c). As described with the embodiment above, when the immunochromatographic test strip 41 is dry, reflected light of the comparatively high intensity P1 is detected by the photodetecting element 82. When the sample reaches the first position (band-like region 41c), because the absorbance increases, the intensity of the light reflected to the photodetecting element 82 changes to an intensity P2 (<P1). The controller 15 observes the change of absorbance based on the electrical signal from the photodetecting element 82 (step S44) and starts timing at the time to at which the absorbance changed (step S45). After sensing the change of absorbance at the first position (band-like region 41c), the controller 15 turns off the light emitting element 81.

Figure 30:
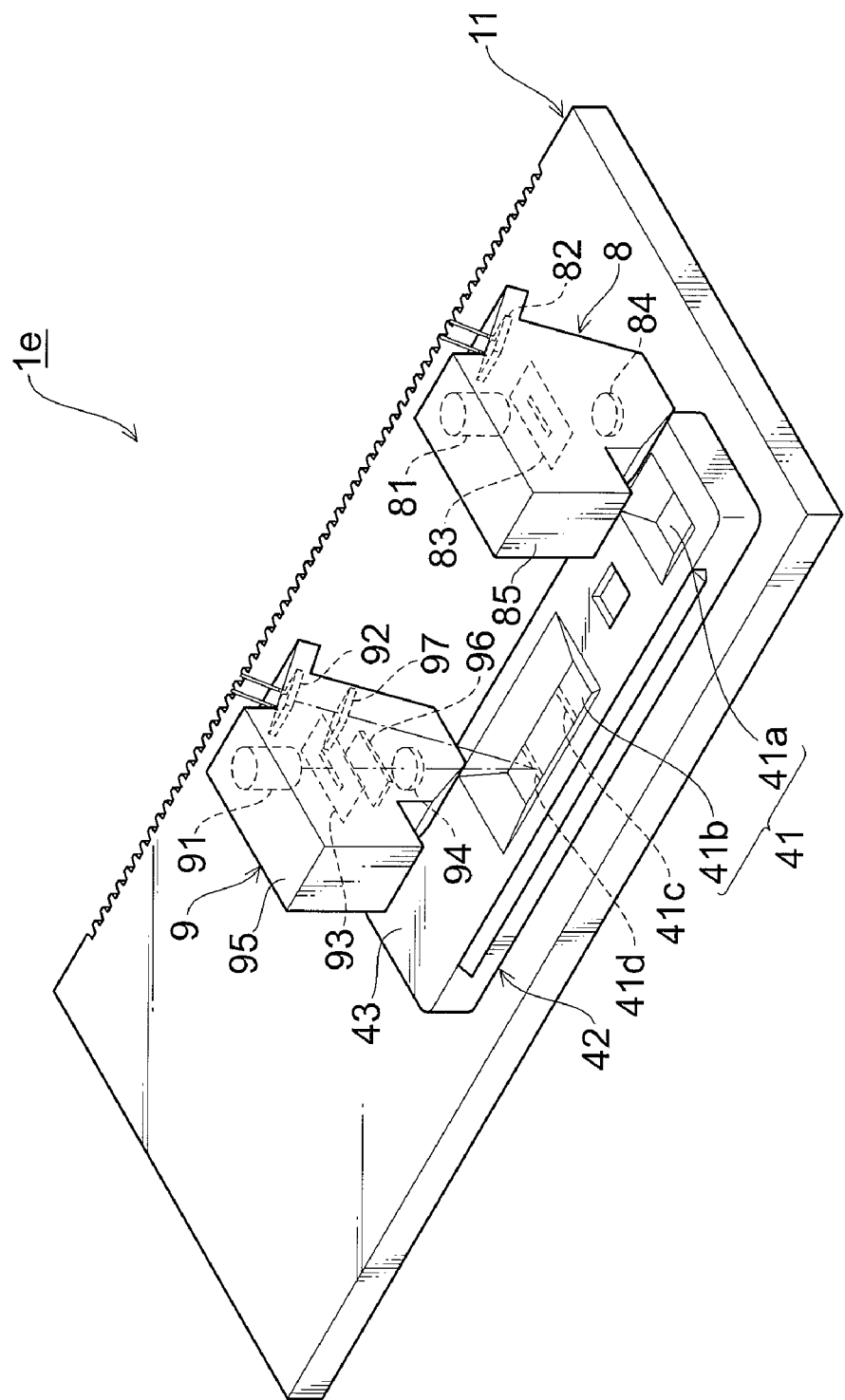
FIG. 30 is a perspective view for describing an operating state of the measuring apparatus of the third embodiment.

Subsequently, the controller 15 moves the setting plate 11 and the optical head 9 in a relative manner so as to detect the fluorescence from a second position on the immunochromatographic test strip 41 at a downstream side of the first position. Specifically, the controller 15 moves the setting plate 11 by actuating the drive mechanism 12 again and thereby controls the relative positional relationship of the optical head 9 and the immunochromatographic test strip 41 so that the second position on the immunochromatographic test strip 41 is positioned in a light emitting direction of the light emitting element 91 of the optical head 9 (step S46). In the present embodiment, the second position on the immunochromatographic test strip 41 is set inside the second band-like region 41d. Thus, as shown in FIG. 30, the band-like region 41d is positioned in the light emitting direction of the light emitting element 91. Thereafter, the controller 15 lights the light emitting element 91, and the light emitting element 91 illuminates the measurement light (excitation light) on the second position (that is, the band-like region 41d) of the immunochromatographic test strip 41. The photodetecting element 92 receives the fluorescence resulting from excitation by the measurement light and converts it to an electrical signal that is in accordance with the fluorescence intensity. The electrical signal is transmitted to the controller 15, and based on this electrical signal, the controller 15 senses the fluorescence intensity at the second position (band-like region 41d) (step S47).

FIG. 33(b) is a schematic graph showing a manner of change of an optical characteristic (fluorescence intensity) at the second position (band-like region 41d). In FIG. 15(b), the ordinate indicates the fluorescence intensity at the second position (band-like region 41d) and the abscissa indicates time. Until the sample reaches the second position (band-like region 41d), only light of an extremely low intensity P3 is detected by the photodetecting element 92 because a fluorescent substance is practically non-present at that position. When the sample reaches the second position (band-like region 41d), because the fluorescent substance labeling the antibody (or antigen) bound to the antigen (or antibody) in the sample is excited by the measurement light, the intensity of fluorescence directed to the photodetecting element 92 changes to an intensity P4 (>P3). The controller 15 observes the change of fluorescence intensity based on the electrical signal from the photodetecting element 92 (step S48) and acquires a difference between the time tb at which the fluorescence intensity changed and the time to (tb−ta), that is, the elapsed time from the change of reflected intensity at the first position (band-like region 41c) to the change of fluorescence intensity at the second position (band-like region 41d) (step S49). After the fluorescence intensity has changed at the second position (band-like region 41d), the controller 15 turns off the light emitting element 91 once.

Then, using the time ta as a reference, the controller 15 performs counting of a predetermined time (step S50). During this predetermined time, the abovementioned first and second antigen-antibody reactions proceed and the reaction lines TL and CL become expressed at the band-like regions 41c and 41d. This predetermined time is set longer than the abovementioned elapsed time (tb−ta), for example, to approximately 15 minutes and adjusted as suited according to the type of the sample.

Figure 31:
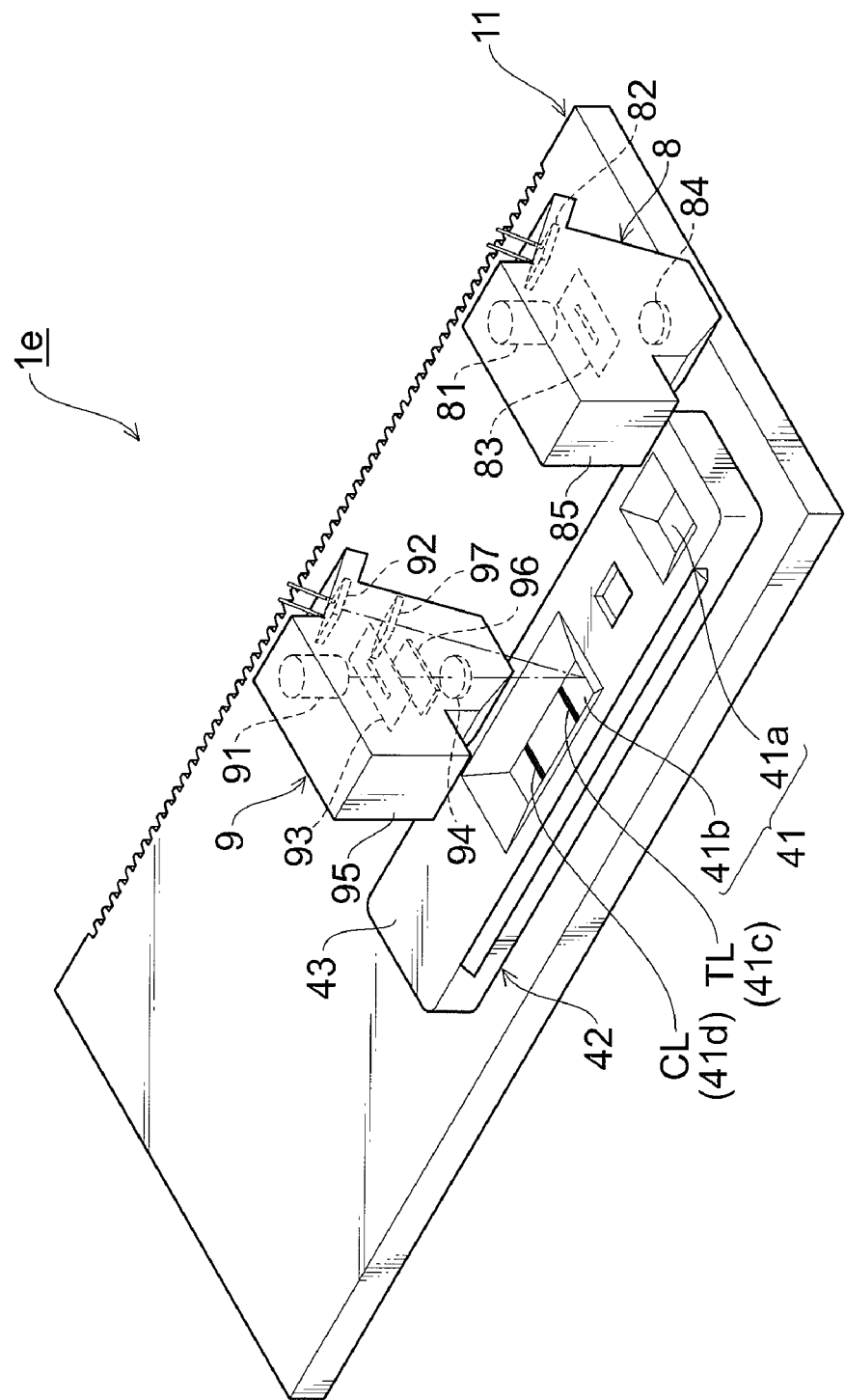
FIG. 31 is a perspective view for describing an operating state of the measuring apparatus of the third embodiment.
Figure 32:
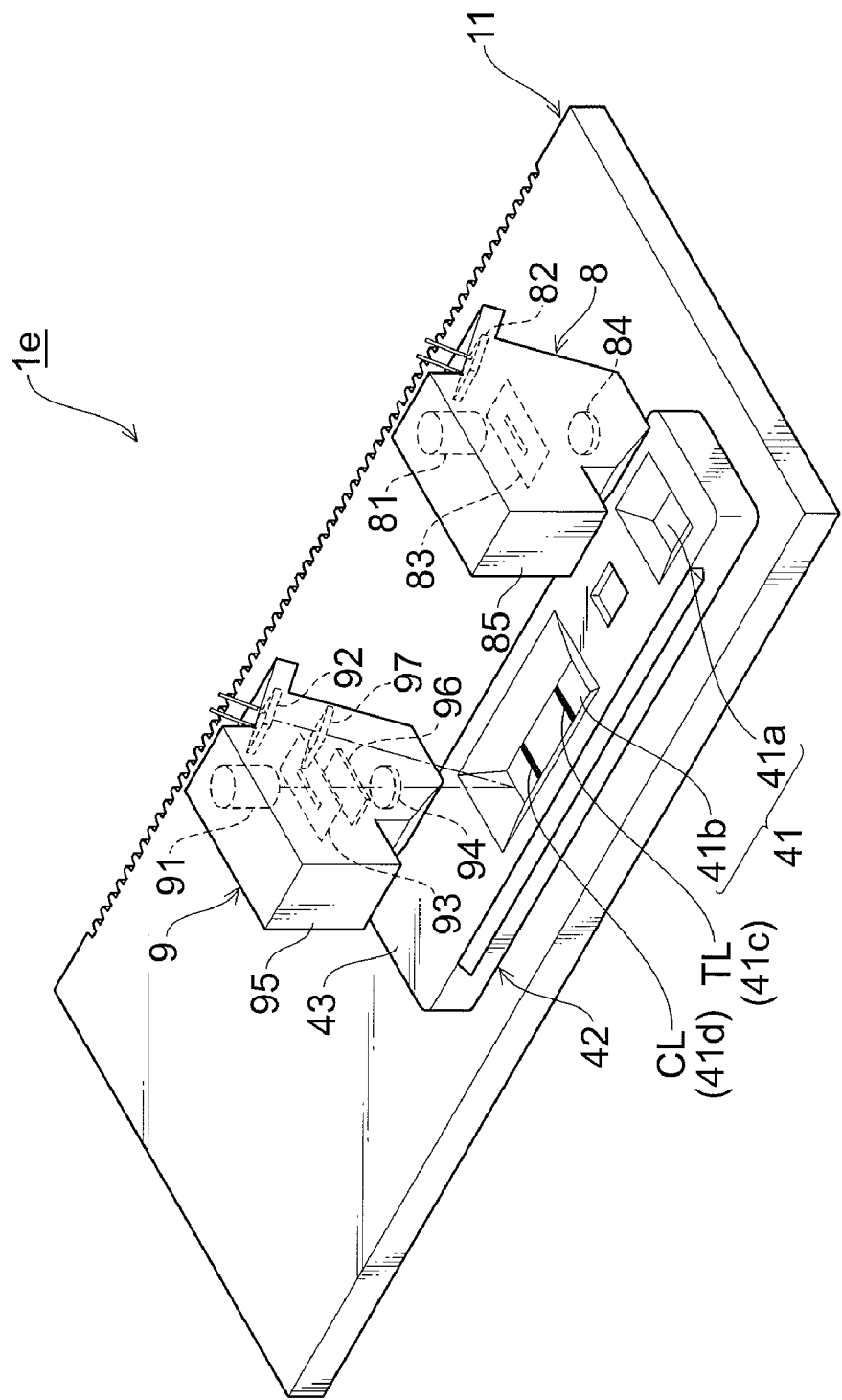
FIG. 32 is a perspective view for describing an operating state of the measuring apparatus of the third embodiment.

After the elapse of the predetermined time from the time ta, the controller 15 relights the light emitting element 91, and while scanning the measurement light of the light emitting element 91 in the sample flow direction so that the illumination position of the measurement light passes through the band-like regions 41c and 41d, detects the fluorescence by the photodetecting element 92 continuously (or intermittently), and obtains a fluorescence profile in the detection portion 41b (step S51). Specifically, the controller 15 actuates the drive mechanism 12 again to move the setting plate 11 and makes the end at the upstream side of the detection portion 41b be positioned in the light emitting direction of the light emitting element 91 as shown in FIG. 31. Then, while moving the illumination position of the measurement light toward the downstream side (that is, while moving the immunochromatographic test strip 41 to the upstream side relative to the optical head 9) until the end at the downstream side of the detection portion 41b is positioned in the light emitting direction of the light emitting element 91 (see FIG. 32), the controller 15 makes the light emitting element 91 illuminate the measurement light and acquires the electrical signal that is in accordance with the fluorescence intensity by the photodetecting element 92.

Figure 34:
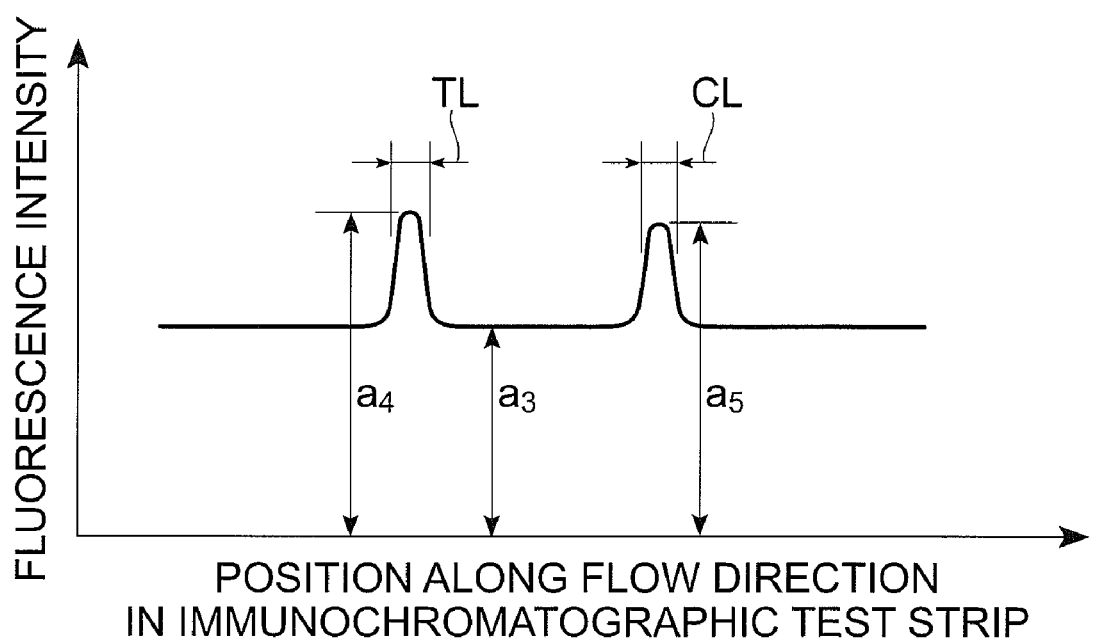
FIG. 34 is a diagram of an example of a fluorescence profile.

FIG. 34 is a diagram of an example of a fluorescence profile obtained by the above-described operation. In FIG. 34, the ordinate indicates the fluorescence intensity and the abscissa indicates the position on the detection portion 41b in the sample flow direction. The controller 15 prepares the fluorescence profile such as that shown in FIG. 34, and from the fluorescence profile, computes a fluorescence $PL_1$ of the test line TL and a fluorescence $PL_2$ of the control line CL on the immunochromatographic test strip 41 by the computation formulae: $PL_1=\log(a_4/a_3)$; and $PL_2=\log(a_5/a_3)$; respectively. The fluorescences $PL_1$ and $PL_2$ express the respective reaction degrees of the reaction lines TL and CL. Based on a relationship formula set in advance, the controller 15 corrects the fluorescences $PL_1$ and $PL_2$ according to the time (tb−ta). The controller 15 judges success or failure of measurement based on the corrected fluorescence $PL_2$ of the control line CL, and references a calibration curve diagram prepared in advance to determine a total amount (concentration) of the antigen (or antibody) contained in the sample in accordance with the corrected fluorescence $PL_1$ of the test line TL and outputs this by a display device, printer, or other output device (step S52).

The reaction degrees of the test line TL and the control line CL formed in the detection portion 41b of the immunochromatographic test strip 41 are thus measured by the measuring apparatus 1e of the present embodiment.

With the measuring method according to the present embodiment described above, by sensing the change of absorbance at the first position (band-like region 41c) on the immunochromatographic test strip 41 by detecting the reflected light while illuminating the measurement light on the first position (band-like region 41c) and sensing the change of fluorescence intensity at the second position (band-like region 41d) by detecting the fluorescence while illuminating the measurement light on the second position (band-like region 41d), the timings ta and tb at which the sample reaches the respective positions can be known readily. By then correcting the fluorescences (reaction degrees) of the reaction lines TL and CL based on the elapsed time (tb−ta, that is, the flow speed of the sample) from the change of absorbance at the first position (band-like region 41c) to the change of fluorescence intensity at the second position (band-like region 41d), the influence due to the fluctuation of reaction degree can be suppressed and the amount of the antigen (or antibody) in the sample can be analyzed with good precision.

The following modification is possible with the measuring apparatus 1e according to the present embodiment. That is, the same wavelength filters as the wavelength filters 96 and 97 of the optical head 9 may be disposed in the optical head 8 so that not reflected light but fluorescence is detected at the photodetecting element 82. Even with such a configuration, the timing ta at which the sample reaches the first position (band-like region 41c) can be made known favorably. That is, the fluorescent substance is developed along with the sample in the immunochromatographic test strip 41, and when a position reached by the sample is excited by the measurement light, fluorescence is generated and because the sample absorbs the measurement light at the same time, the absorbance decreases. The timings ta and tb can thus be made known by detecting one of either the reflected light or the fluorescence at the optical heads 8 and 9.

The following modification is furthermore possible with the measuring apparatus 1e according to the present embodiment. That is, as in the measuring apparatus 1b according to the second embodiment, acquisition of the timings ta and tb and measurement of the reaction degrees may be performed using a single optical head. In this case, the measuring apparatus has a configuration in which the optical head 8 of the present embodiment is excluded. That is, this measuring apparatus includes: the light emitting element (light illuminating unit) 91, illuminating the measurement light on the immunochromatographic test strip 41, on which a sample is dropped; the photodetecting element (photodetecting unit) 92, detecting the fluorescence from the immunochromatographic test strip 41 due to illumination of the measurement light; the setting plate (test strip support) 11, supporting the immunochromatographic test strip 41; the drive mechanism 12, moving the setting plate 11 and the photodetecting element 92 in a relative manner in the sample flow direction of the immunochromatographic test strip 41; and the controller 15, controlling the drive mechanism 12.

The controller 15 moves the setting plate 11 and the photodetecting element 92 in a relative manner to detect the fluorescence from the first position (band-like region 41c) on the immunochromatographic test strip 41, thereafter moves the setting plate 11 and the photodetecting element 92 in a relative manner to detect the fluorescence from the second position (band-like region 41d), and, based on the output signals from the photodetecting element 92, acquires the elapsed time from the change of fluorescence intensity at the first position (band-like region 41c) to the change of fluorescence intensity at the second position (band-like region 41d). By this configuration, because the changes of fluorescence intensity at the respective positions can be sensed favorably, the timings ta and tb at which the sample reaches the respective positions can be made known.

The present invention is not restricted to the respective embodiments and modification examples described above. For example, as the light illuminating unit, a laser diode or other semiconductor light emitting element may be used in place of the light emitting diode. Also, as the photodetecting unit, in place of the Si photodiode, a phototransistor or other semiconductor light receiving element, a CCD, or a photoelectric tube, a photomultiplier tube, or other vacuum tube type photosensor may be used.

Also, with the respective embodiments described above, the first position in the immunochromatographic test strip 41 is set in the band-like region 41c that is to be the test line TL and the second position is set in the band-like region 41d that is to be the control line CL. The first and second positions in the present invention are not restricted to these and may be set to any positions on the immunochromatographic test strip.

Also, although with the embodiments described above, in regard to the correlation of the coloration degree and the flow speed of the sample, the correlation shown in FIG. 16 such that the longer the time (tb−ta), the higher the absorbance $ABS_1$ was described as an example, the correlation between the two is not restricted thereto. For example, even with a correlation such that the absorbance $ABS_1$ becomes lower the longer the time (tb−ta), by correcting the reaction degrees at the lines TL and CL based on the time (tb−ta), the influence of the fluctuation of reaction degree can be suppressed and the amount of an antigen (or antibody) in a sample can be analyzed with good precision with the measuring method according to the present invention.

Also, although with the respective embodiments described above, the drive mechanism moves the sample strip support (setting plate 11) to move the immunochromatographic test strip and the light illuminating unit in a relative manner, the sample strip support may be fixed and the drive mechanism may move the light illuminating unit to move the immunochromatographic test strip and the light illuminating unit in a relative manner. Or, the drive mechanism may move both the test strip support and the light illuminating unit to move the immunochromatographic test strip and the light illuminating unit in a relative manner.

The invention claimed is:

1. A method for measuring immunochromatographic test strip, wherein light obtained from an immunochromatographic test strip by illumination of measurement light is detected to measure a reaction degree of an antigen-antibody reaction, the method comprising the steps of:
sensing a change of optical characteristic at a first position on the immunochromatographic test strip by detecting light from the immunochromatographic test strip while illuminating measurement light on the first position after dropping a sample onto the immunochromatographic test strip; sensing a change of optical characteristic at a second position at a downstream side of the first position on the immunochromatographic test strip by detecting light from the immunochromatographic test strip while illuminating measurement light on the second position; and acquiring an elapsed time from the change of optical characteristic at the first position to the change of optical characteristic at the second position; and
measuring the reaction degree of the antigen-antibody reaction at the first position on the basis of the optical characteristic at the first position after elapse of a predetermined time, longer than the elapsed time, from the change of optical characteristic at the first position,
wherein the reaction degree is corrected on the basis of a correlation of the elapsed time and the optical characteristic at the first position after the elapse of the predetermined time.

2. A method for measuring immunochromatographic test strip, wherein measurement light is illuminated on an immunochromatographic test strip and reflected light is detected to measure a coloration degree of a colored line, the method comprising the steps of:
sensing a change of absorbance at a first position of a first colored line on the immunochromatographic test strip by detecting reflected light while illuminating measurement light on the first position after dropping a sample onto the immunochromatographic test strip; sensing a change of absorbance at a second position of a second colored line at a downstream side of the first colored line on the immunochromatographic test strip by detecting reflected light while illuminating measurement light on the second position; and acquiring an elapsed time from the change of absorbance at the first position to the change of absorbance at the second position; and
measuring the coloration degree at the first position on the basis of the absorbance at the first position after elapse of a predetermined time, longer than the elapsed time, from the change of absorbance at the first position, wherein the coloration degree is corrected on the basis of a correlation of the elapsed time and the absorbance at the first position after the lapse of the predetermined time.

3. The method for measuring immunochromatographic test strip according to claim 2, wherein the immunochromatographic test strip has at least one band-like region causing an antigen-antibody reaction with the sample, and the measurement light is scanned in a sample flow direction to measure the absorbance at the first position so that an illumination position of the measurement light passes through the band-like region after elapse of a predetermined time, longer than the elapsed time, from the change of absorbance at the first position.

4. The method for measuring immunochromatographic test strip according to claim 3, wherein the measurement light is turned off after the change of absorbance at the second position and is relit thereafter to perform scanning after elapse of the predetermined time.

5. The method for measuring immunochromatographic test strip according to claim 2, wherein the immunochromatographic test strip has a first band-like region, causing a first antigen-antibody reaction, and a second band-like region, disposed at a downstream side of the first band-like region and causing a second antigen-antibody reaction, and the first position is disposed inside the first band-like region and the second position is disposed inside the second band-like region.

6. A method for measuring immunochromatographic test strip, wherein measurement light is illuminated on an immunochromatographic test strip containing a fluorescent substance and a fluorescence intensity of a reaction line excited by the measurement light is detected to measure a reaction degree of an antigen-antibody reaction at the reaction line, the method comprising the steps of:

sensing a change of absorbance or a change of fluorescence intensity at a first position of a first reaction line on the immunochromatographic test strip by detecting reflected light or fluorescence while illuminating measurement light on the first position after dropping the sample onto the immunochromatographic test strip;

sensing a change of absorbance or a change of fluorescence intensity at a second position of a second reaction line at a downstream side of the first reaction line on the immunochromatographic test strip by detecting reflected light or fluorescence while illuminating measurement light on the second position; and acquiring an elapsed time from the change of absorbance or fluorescence intensity at the first position to the change of absorbance or fluorescence intensity at the second position; and measuring the reaction degree of the antigen-antibody reaction at the first position on the basis of the fluorescence intensity at the first position after elapse of a predetermined time, longer than the elapsed time, from the change of absorbance or fluorescence intensity at the first position, wherein the reaction degree is corrected on the basis of a correlation of the elapsed time and the fluorescence intensity at the first position after the elapse of the predetermined time.

* * * * *